US009782057B2

(12) United States Patent
Kasumi et al.

(10) Patent No.: US 9,782,057 B2
(45) Date of Patent: Oct. 10, 2017

(54) THREE-DIMENSIONAL IMAGE SYSTEM FOR MULTIPLE 3D DISPLAY

(71) Applicant: OLYMPUS CORPORATION, Tokyo (JP)

(72) Inventors: Makoto Kasumi, Hachioji (JP); Masashi Umemura, Hamburg (DE); Shusuke Tsuchiya, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/076,222

(22) Filed: Mar. 21, 2016

(65) Prior Publication Data
US 2016/0205387 A1 Jul. 14, 2016

Related U.S. Application Data

(63) Continuation of application No. PCT/JP2014/075100, filed on Sep. 22, 2014.

(30) Foreign Application Priority Data

Oct. 2, 2013 (JP) .................................. 2013-207455

(51) Int. Cl.
H04N 9/47 (2006.01)
A61B 1/00 (2006.01)
(Continued)

(52) U.S. Cl.
CPC ...... *A61B 1/00193* (2013.01); *A61B 1/00009* (2013.01); *G09G 5/00* (2013.01);
(Continued)

(58) Field of Classification Search
CPC .................................................. A61B 1/00193
(Continued)

(56) References Cited

U.S. PATENT DOCUMENTS 5,751,341 A 5/1998 Chaleki et al.
6,636,254 B1 10/2003 Onishi et al.
(Continued)

FOREIGN PATENT DOCUMENTS

EP 0 655 710 A2 5/1995
JP H01-158377 A 6/1989
(Continued)

OTHER PUBLICATIONS

Dec. 16, 2014 Search Report issued in International Patent Application No. PCT/JP2014/075100.
(Continued)

*Primary Examiner* — Richard Torrente
(74) *Attorney, Agent, or Firm* — Oliff PLC

(57) ABSTRACT

A three-dimensional image system includes a monitor that displays an image signal as an image for three-dimensional observation, glasses for three-dimensional observation for observing, as a three-dimensional image, the image for three-dimensional observation displayed on a display section of the monitor, a storing section that is provided in the glasses for three-dimensional observation and stores an image parameter correction value for three-dimensional observation for correcting image parameters for three-dimensional observation for giving a cubic effect of the image for three-dimensional observation displayed on the display section, a scanning section that scans the glasses for three-dimensional observation in order to read information stored in the storing section, and a control section that performs control to set, according to a scanning result of the scanning section, the image parameter correction value for three-dimensional observation in the monitor.

10 Claims, 16 Drawing Sheets

(51) Int. Cl.
 H04N 13/00 (2006.01)
 H04N 13/04 (2006.01)
 G09G 5/00 (2006.01)
 G09G 5/36 (2006.01)
 H04N 13/02 (2006.01)

(52) U.S. Cl.
 CPC ........... G09G 5/36 (2013.01); H04N 13/0022 (2013.01); H04N 13/0037 (2013.01); H04N 13/0044 (2013.01); H04N 13/0059 (2013.01); H04N 13/0429 (2013.01); H04N 13/0497 (2013.01); *H04N 13/0239* (2013.01); *H04N 13/0253* (2013.01); *H04N 13/047* (2013.01); *H04N 13/0438* (2013.01); *H04N 13/0475* (2013.01); *H04N 2213/008* (2013.01)

(58) Field of Classification Search
 USPC .......................................................... 348/53
 See application file for complete search history.

(56) References Cited

U.S. PATENT DOCUMENTS

| | | | | |
|---|---|---|---|---|
| 2008/0239063 | A1* | 10/2008 | Ishikawa | ............ G02B 23/2415 348/46 |
| 2011/0216175 | A1 | 9/2011 | Shimoyama et al. | |
| 2012/0081527 | A1* | 4/2012 | Richardson | ........ H04N 13/0497 348/56 |
| 2012/0169852 | A1* | 7/2012 | Seo | .................... H04N 13/0497 348/56 |
| 2013/0155055 | A1* | 6/2013 | Doi | ........................ G06T 15/00 345/419 |
| 2013/0235167 | A1 | 9/2013 | Izawa et al. | |

FOREIGN PATENT DOCUMENTS

| | | |
|---|---|---|
| JP | H07-265264 A | 10/1995 |
| JP | H11-164329 A | 6/1999 |
| JP | 2011-188118 A | 9/2011 |
| JP | 2012-195923 A | 10/2012 |
| JP | 2013-055383 A | 3/2013 |
| JP | 2013-192168 A | 9/2013 |

OTHER PUBLICATIONS

Jul. 7, 2015 Office Action issued in Japanese Patent Application No. 2015-515342.

May 30, 2017 Search Report issued in European Patent Application No. 14851044.9.

* cited by examiner

FIG. 2
(A)
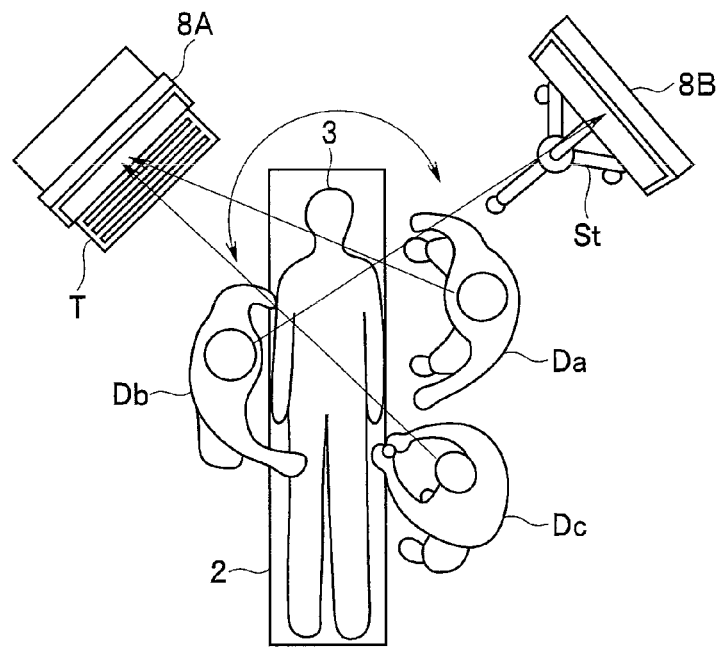
(B)
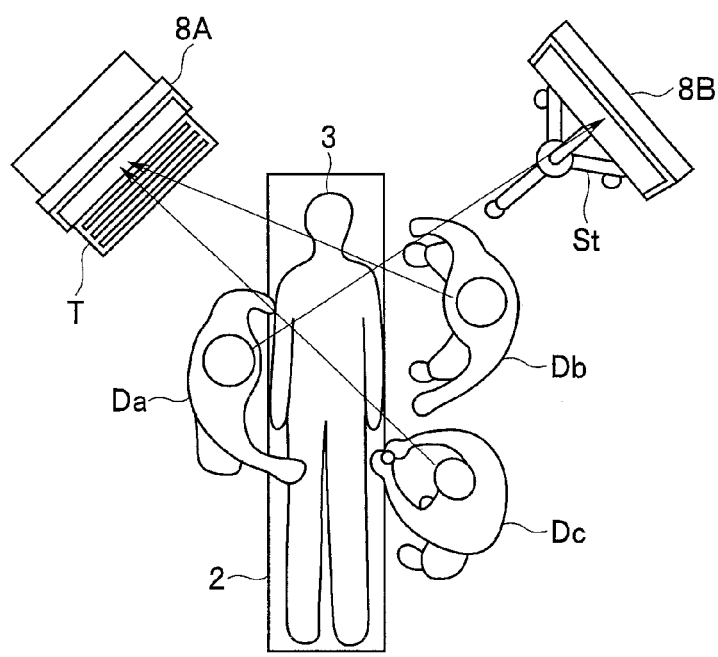

FIG. 8
(A)
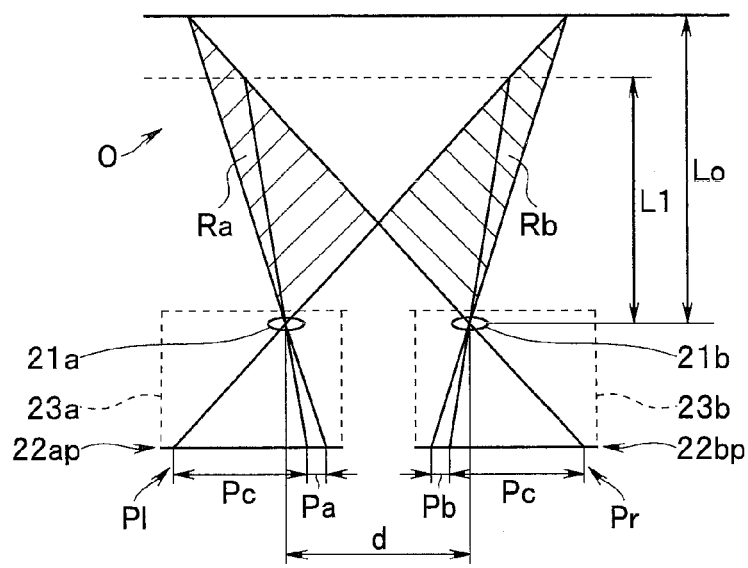
(B)
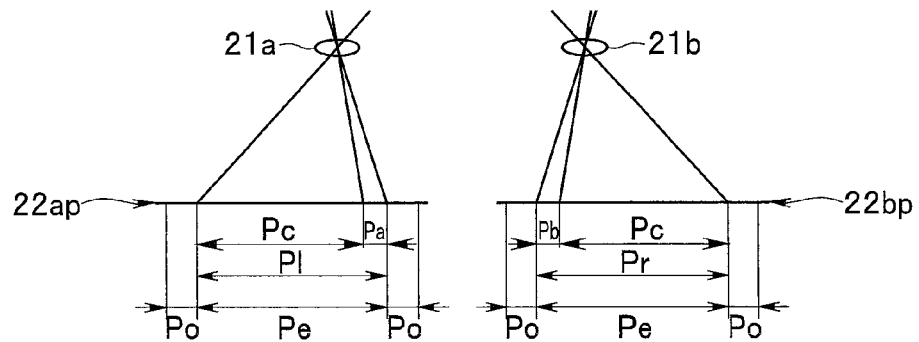
(C)
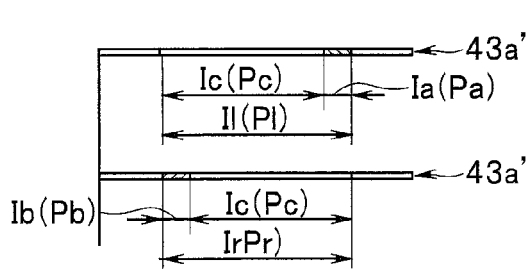
(D)
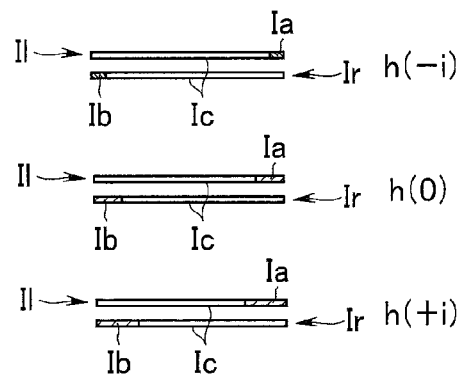

FIG. 10

| 3D GLASSES ID | MONITOR SIZE (INCHES) | SURGEON PRIORITY | DEPTH AMOUNT CORRECTION VALUE | COLOR TONE CORRECTION VALUE | COLOR MODE |
|---|---|---|---|---|---|
| OOOOO | 19 | B | +1 | (−,+3,−) | O |
| | 26 | B | +3 | (−,+3,−) | O |
| | 32 | B | +5 | (−,+3,−) | O |

THREE-DIMENSIONAL IMAGE SYSTEM FOR MULTIPLE 3D DISPLAY

CROSS REFERENCE TO RELATED APPLICATION

This application is a continuation application of PCT/JP2014/075100 filed on Sep. 22, 2014 and claims benefit of Japanese Application No. 2013-207455 filed in Japan on Oct. 2, 2013, the entire contents of which are incorporated herein by this reference.

BACKGROUND OF THE INVENTION

1. Field of the Invention

The present invention relates to a three-dimensional image system for observing an image for three-dimensional observation displayed on a monitor.

2. Description of the Related Art

In recent years, endoscopes have been widely used in a medical field. A normal endoscope includes one image pickup apparatus. The one image pickup apparatus picks up a two-dimensional image. The two-dimensional image is displayed on a monitor. A surgeon performs an endoscopic test, a surgical operation, and the like while observing the two-dimensional image displayed on the monitor.

When a surgical operation is performed, a three-dimensional image system is sometimes adopted that uses a stereoscopic endoscope or a three-dimensional endoscope including two image pickup apparatuses and displays, on a monitor, an image for three-dimensional observation generated from two-dimensional images having a parallax. The surgeon can visually recognize (observe) the image for three-dimensional observation as a three-dimensional image having a cubic effect or a depth feeling by wearing glasses for three-dimensional observation and observing the image for three-dimensional observation.

In such a three-dimensional image system, the surgeon can observe the image for three-dimensional observation as the three-dimensional image having a cubic effect or a depth feeling. Therefore, the surgeon can easily recognize unevenness of a diseased part and a depth feeling on a distal end side of a treatment instrument. It is possible to perform the surgical operation smoothly and in a short time.

Japanese Patent Application Laid-Open Publication No. 11-164329 serving as a first conventional example discloses a stereoscopic-video display apparatus in which parallax-amount controlling means controls, according to setting information from setting controlling means, a parallax amount of image signals for left and right eyes for performing stereoscopic display.

Japanese Patent Application Laid-Open Publication No. 2011-188118 serving as a second conventional example discloses a stereoscopic display apparatus capable of performing stereoscopic display when a viewer views, using glasses, a display image displayed on a display section. In the apparatus, the glasses transmit attribute information of the glasses to the display apparatus side. The display apparatus reads out, from a storing section, parameter information corresponding to the attribute information of the glasses received by a receiving section. A control section generates image control information according to the parameter information. An adjusting section adjusts a display image on the basis of the image control information. A display section displays the adjusted display image. When there are a plurality of viewers, the display images can be adjusted taking into account priority.

In the first conventional example, in order to set the display apparatus to a parallax amount suitable for an observing observer, a position of the observer is detected by detecting means such as a camera provided at the display apparatus, the observer is specified using detected information, and a parallax amount of a video to be displayed is controlled using parallax amount setting information stored in advance in association with the specified observer.

In the second conventional example, the storing section that stores image information for adjusting a cubic effect or a depth feeling is provided on the display apparatus side.

SUMMARY OF THE INVENTION

A three-dimensional image system according to an aspect of the present invention includes: a monitor that displays an image signal as an image for three-dimensional observation; glasses for three-dimensional observation for observing, as a three-dimensional image, the image for three-dimensional observation displayed on a display section of the monitor; a storing section that is provided in the glasses for three-dimensional observation and stores an image parameter correction value for three-dimensional observation for correcting image parameters for three-dimensional observation for giving a cubic effect of the image for three-dimensional observation displayed on the display section; a scanning section that scans the glasses for three-dimensional observation including the storing section in order to read information stored in the storing section; and a control section that performs control to set, according to a scanning result of the scanning section, in the monitor, the image parameter correction value for three-dimensional observation stored in the storing section. The monitor includes first and second display sections disposed in positions different from each other and configuring the display section and first and second monitors respectively including first and second control sections configuring the control section, the storing section provided in the glasses for three-dimensional observation stores first and second image parameter correction values for three-dimensional observation serving as the image parameter correction value for three-dimensional observation used when a first observer wears the glasses for three-dimensional observation and respectively observes the first and second display sections, and the first and second control sections perform control to correct, respectively according to the first and second image parameter correction values for three-dimensional observation, first and second image parameters for three-dimensional observation serving as the image parameters for three-dimensional observation in first and second images for three-dimensional observation serving as the image for three-dimensional observation respectively displayed on the first and second display sections.

BRIEF DESCRIPTION OF THE DRAWINGS

FIG. 2 is a schematic diagram of disposition in top view of a state in which an observed monitor changes according to a change in positions of a plurality of surgeons during a surgical operation;

FIG. 8 is an explanatory diagram of a state in which images of an object are picked up by two image pickup sections a distance d apart from each other in a left-right direction, a state in which picked-up left and right images are schematically displayed, a depth amount for giving a cubic effect, and the like;

FIG. 10 is a diagram showing, in a table format, an example of data written in the 3D glasses;

DETAILED DESCRIPTION OF THE PREFERRED EMBODIMENTS

Embodiments of the present invention are explained below with reference to the drawings.

First Embodiment

Figure 1:
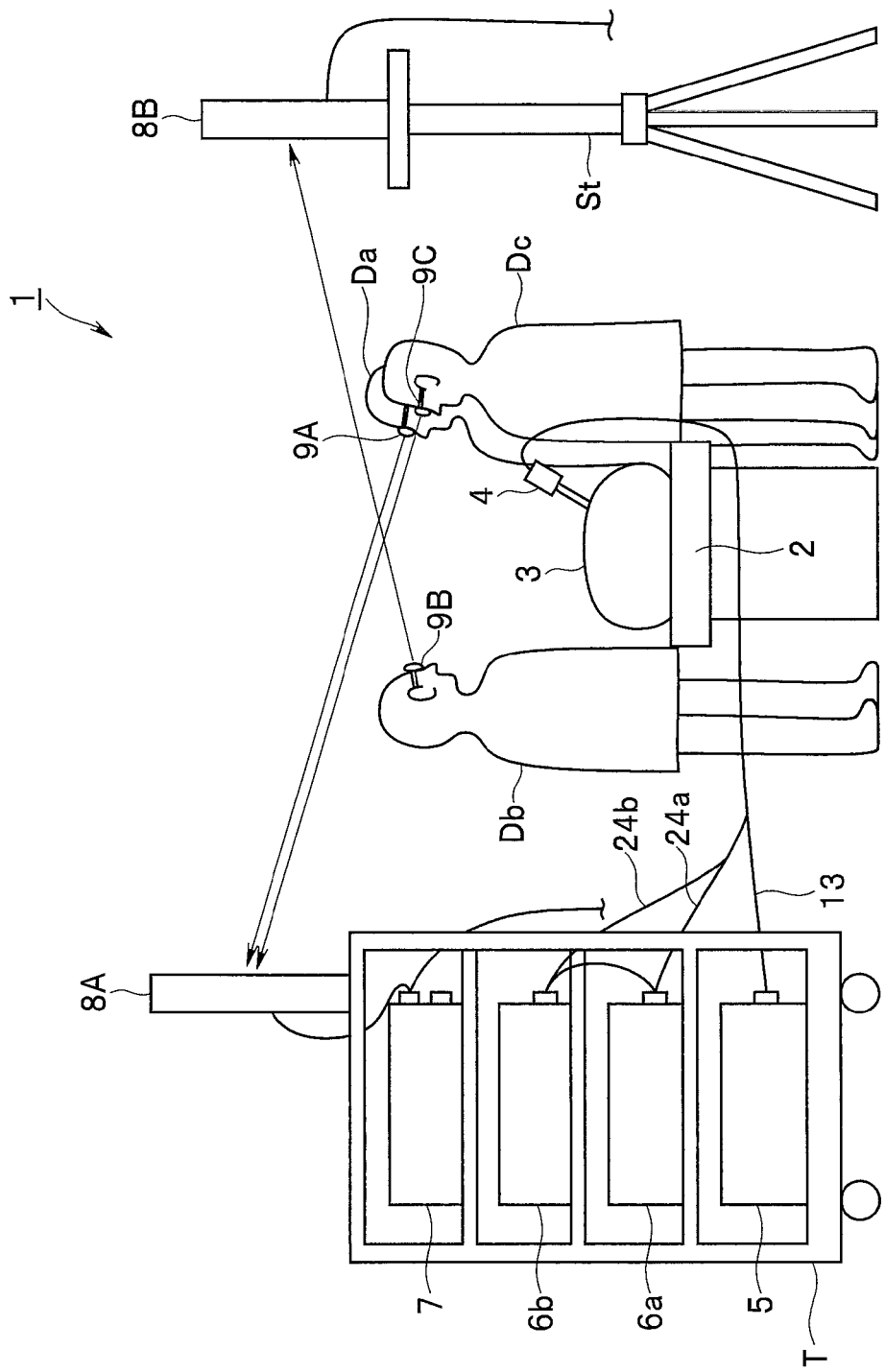
FIG. 1 is a diagram showing an overall configuration of a three-dimensional image system in a first embodiment of the present invention.

As shown in FIG. 1 or FIG. 2, a three-dimensional image system 1 in a first embodiment of the present invention is operated on a patient 3 lying on a bed 2 in an endoscopic test room or an operating room by at least one of a plurality of observers (who uses the three-dimensional image system 1), for example, an operating doctor Da (hereinafter, first surgeon) who, for example, leads a surgical operation, an assistant doctor Db (hereinafter, second surgeon) who performs the surgical operation assisting the first surgeon acting as the operating doctor Da, and an endoscope doctor Dc (hereinafter, third surgeon) who operates, for example, an endoscope. Note that, in FIG. 1 and FIG. 2, three surgeons are shown. However, the three-dimensional image system 1 can also be applied in the case of one or two surgeons. FIG. 2(A) and FIG. 2(B) show, as schematic diagrams in top view, a state in which positions of the first surgeon Da, the second surgeon Db, and the third surgeon Dc change during a surgical operation and an observed monitor changes according to the change in the positions.

The three-dimensional image system 1 includes a stereoscopic endoscope or a three-dimensional endoscope (abbreviated as 3D endoscope) 4 used for a stereoscopic observation, a light source apparatus 5, a first processor 6A that generates a video signal (or an image signal) for a left eye, a second processor 6B that generates a video signal (or an image signal) for a right eye, a three-dimensional mixer (abbreviated as 3D mixer) 7 functioning as an image generating apparatus that generates a three-dimensional (3D) video signal (or image signal) for a stereoscopic (3D) observation from the first and second video signals (or image signals) outputted from the processors 6A and 6B, a first monitor 8A that displays the 3D video signal (or image signal) generated by the 3D mixer 7 disposed on a trolley (or a cart) T, a second monitor 8B attached to a stand St, and 3D glasses 9A, 9B, and 9C that the first to third surgeons Da to Dc respectively use in order to perform a stereoscopic observation of the first monitor 8A or the second monitor 8B.

Figure 3:
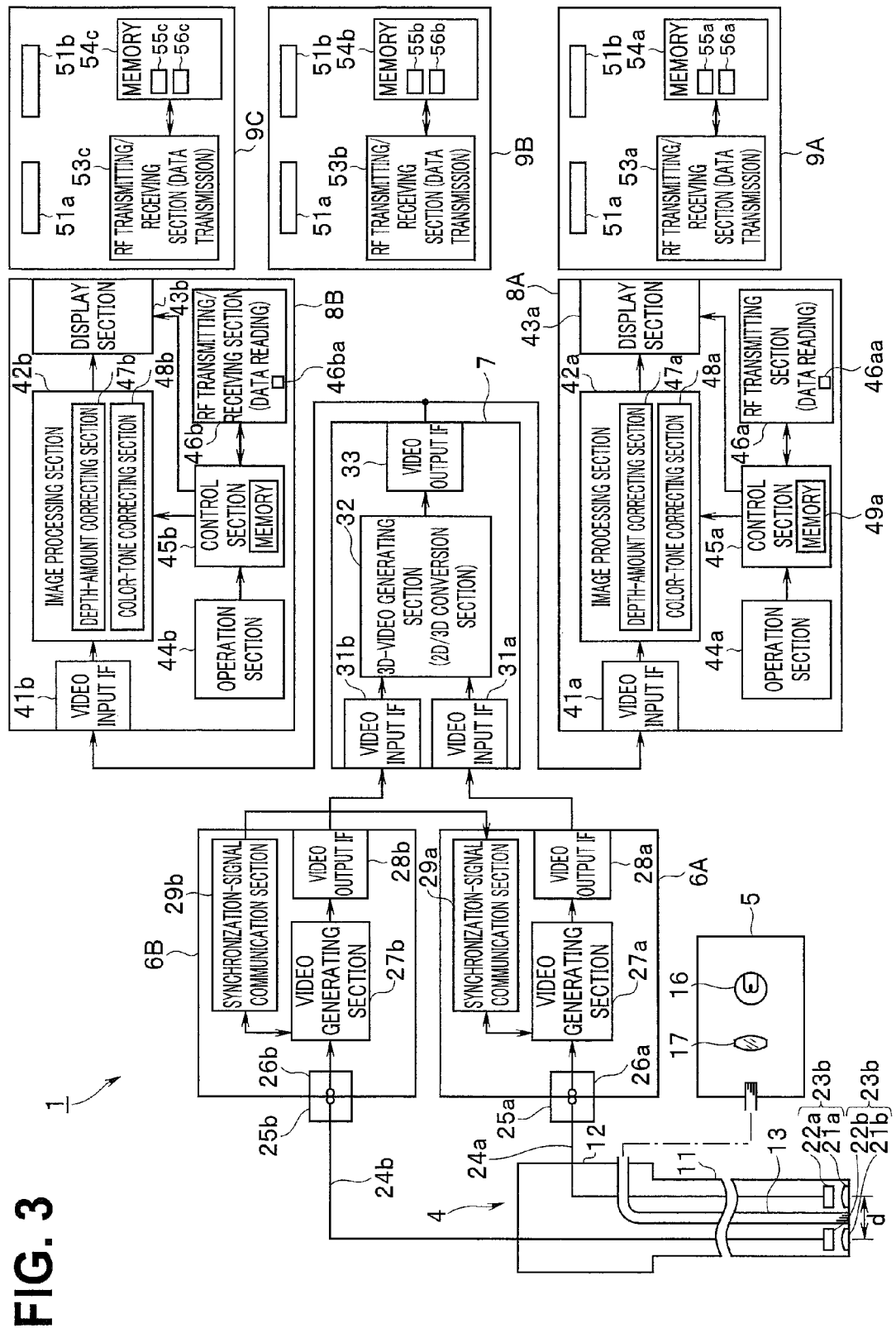
FIG. 3 is a diagram showing an internal configuration of the three-dimensional image system.

FIG. 3 shows an internal configuration of the endoscope 4 and the like configuring the three-dimensional image system 1. The endoscope 4 includes an insertion section 11 inserted into a body, a grasping section 12 provided at a rear end (a proximal end) of the insertion section 11 and grasped by, for example, the third surgeon Dc, and a light guide 13 and a signal cable 14 extended from the grasping section 12. An end portion of the light guide 13 is detachably connected to the light source apparatus 5.

The light source apparatus 5 includes a lamp 16 that generates white illumination light and a condensing lens 17 that condenses the illumination light and makes the illumination light incident on (supplies the illumination light to) the end portion of the light guide 13. The illumination light made incident on the end portion of the light guide 13 is transmitted to an end portion on a distal end side of the light guide 13 inserted through the insertion section 11. The illumination light is emitted from a distal end face of the light guide 13 to illuminate an object such as a diseased part in a body.

At a distal end portion of the insertion section 11, an objective lens for left eye 21a and an objective lens for right eye 21b for forming optical images of an object are disposed a distance d apart from each other in a left-right direction. An image pickup surface of a charge coupled device (abbreviated as CCD) for left eye 22a functioning as an image pickup device for left eye and an image pickup surface of a CCD for right eye 22b functioning as an image pickup device for right eye are disposed in image forming positions of the objective lens for left eye 21a and the objective lens for right eye 21b.

The CCDs 22a and 22b output image pickup signals serving as output signals obtained by photoelectrically converting the formed optical images. An image pickup section for left eye (an image pickup apparatus for left eye) or a left image pickup section (a left image pickup apparatus) 23a is formed by the objective lens for left eye 21a and the CCD for left eye 22a. An image pickup section for right eye (an image pickup apparatus for right eye) or a left image pickup section (a left image pickup apparatus) 23b is formed by the objective lens for right eye 21b and the CCD for right eye 22b. Images of the same object is picked up by the image pickup sections 23a and 23b having the distance d and different visual line directions and displayed as a 3D observation image on a display apparatus monitor, whereby a surgeon (acting as an observer) observing the 3D observation image can sense a cubic effect or a depth feeling and observe respective sections in the object.

A signal connector 25a at a rear end of the CCD 22a is detachably connected to a signal connector receiver 26a of the first processor 6A via a signal line 24a inserted through the endoscope 4. A signal connector 25b at a rear end of the CCD 22b is detachably connected to a signal connector receiver 26b of the second processor 6B via a signal line 24b inserted through the endoscope 4.

The first processor 6A includes a video generating section (or a video generation circuit) 27a that generates a two-dimensional (2D) video signal (or an image signal) for the left eye from an image pickup signal for the left eye generated by the CCD 22a, a video output interface (a video output IF) 28a that outputs a 2D video signal generated by the video generating section 27a, and a synchronization-signal communication section (or a synchronization-signal communication circuit) 29a that performs communication of a synchronization signal when a video signal (an image signal) is generated. The 2D video signal for the left eye generated by the video generating section 27a is outputted to the 3D mixer 7 via a video output interface 28a.

Similarly, the second processor 6B includes a video generating section (or a video generation circuit) 27b that generates a two-dimensional (2D) video signal (or image signal) for the right eye from an image pickup signal for the right eye generated by the CCD 22b, a video output interface (a video output IF) 28b that outputs the 2D video signal for the right eye generated by the video generating section 27b, and a synchronization-signal communication section (or a synchronization-signal communication circuit) 29b that performs communication of a synchronization signal when a video signal (or an image signal) is generated. The 2D video signal for the right eye generated by the video generating section 27b is outputted to the 3D mixer 7 via the video output interface 28b.

One of the synchronization-signal communication sections 29a and 29b transmits a synchronization signal to the other. The other synchronization-signal communication section, to which the synchronization signal is transmitted, generates a synchronization signal synchronizing with the transmitted synchronization signal. In other words, after performing communication, the synchronization-signal communication sections 29a and 29b change to a state in which the synchronization-signal communication sections 29a and 29b generate the same synchronization signal. The video generating sections 27a and 27b change to a state in which the video generating sections 27a and 27b respectively generate 2D video signals for the left eye and the right eye respectively in synchronization with the same synchronization signal. Note that the video generating sections 27a and 27b may respectively include the video output interfaces 28a and 28b.

The 3D mixer 7 includes video input interfaces (video input IFs) 31a and 31b to which the 2D video signal for the left eye and the 2D video signal for the right eye respectively generated by the video generating sections 27a and 27b are inputted. The 3D mixer 7 includes a 3D-video generating section (or a 3D-video generation circuit) 32 that generates a 3D video signal (or image signal) from the 2D video signal for the left eye and the 2D video signal for the right eye inputted from the video input interfaces 31a and 31b and a video output interface (a video output IF) 33 that outputs the generated 3D video signal (or image signal) to the first 3D monitor 8A and the second 3D monitor 8B functioning as external apparatuses.

The 3D-video generating section 32 compresses, for example, a cycle of the inputted 2D video signals into a half to double a display rate. The 3D-video generating section 32 generates a 3D video signal including a 2D video signal for the left eye in a first frame and including a 2D video signal for the right eye in a second frame. In other words, the 3D-video generating section 32 can also be considered a 2D/3D converting section (or a 2D/3D conversion circuit) that converts the left and right 2D video signals into a 3D video signal.

The first 3D monitor 8A includes a video input interface (a video input IF) 41a to which a 3D video signal is inputted, an image processing section (or an image processing circuit) 42a that performs image processing corresponding to image parameters such as a depth amount correction value on a 3D observation video (or a 3D observation image) displayed on a display section (or a display device) 43a from the inputted 3D video signal (image signal), the display section (or the display device) 43a configured by a liquid crystal display or the like that displays an image signal of the generated 3D observation image, an operation section (an operation device) or an operation input section (an operation input device) 44a that performs setting operation for image processing parameters of the image processing section 42a, a control section (or a control circuit) 45a that performs control of the image processing section 42a and the display section 43a, and an RF transmitting/receiving section (or an RF transmission/reception circuit) 46a that performs transmission and reception with the 3D glasses.

The RF transmitting/receiving section 46a includes a function of a scanning section (or a scanning circuit) 46aa that scans a radio wave in order to detect the 3D glasses. The control section 45a controls the scanning section 46aa included in the RF transmitting/receiving section 46a to perform a scan for periodically detecting the 3D glasses. Note that the scanning section 46aa is configured from, for example, a piezoelectric element to which a main body of the RF transmitting/receiving section 46a is attached and a driving circuit that applies a driving signal to the piezoelectric element. The scanning section 46aa changes a signal level of the driving signal applied to the piezoelectric element to thereby perform transmission and reception of a radio wave to cover an observation range or a scan range substantially equal to the observation range in the case in which the surgeon observes the 3D monitor 8A.

The control section 45a controls the scanning section 46aa to periodically perform a scan for detecting the 3D glasses including the storing section. More specifically, after correcting, according to a depth information correction value stored in a memory (provided in the 3D glasses) configuring the storing section, a 3D observation image on the display section 43a of the 3D monitor 8A, the control section 45a controls the scanning section 46aa to periodically perform the scan for detecting the 3D glasses or the like including the storing section.

In the present embodiment, the 3D video signal (image signal) inputted to the first 3D monitor 8A is directly outputted to the display section 43a. A 3D image of the inputted 3D video signal can be displayed on the display section 43a as a 3D observation video (or a 3D observation image). However, the image processing section 42a inside the first 3D monitor 8A performs image processing for correcting, with an image parameter of a depth amount correction value, a depth amount serving as depth information for substantially determining a degree of a cubic effect such that a 3D observation video (or a 3D observation image) having a cubic effect desired by the surgeon can be displayed. The surgeon observes (visually recognizes) the 3D observation video (or the 3D observation image), which is displayed on the display section 43a, as a 3D image using the 3D glasses.

As explained below, in the present embodiment, when images of the same object are picked up by the left image pickup section 23a and the right image pickup section 23b, in a picked-up image including a common range in which the left image pickup section 23a and the right image pickup section 23b pick up images in common to each other and a left side range and a right side range in which the left image pickup section 23a and the right image pickup section 23b respectively pick up images of only a left side portion and a right side portion in the same object, the control section 45a or 45b corrects the depth amount serving as the depth information for changing and giving a cubic effect by alternately displaying, on the display section 43a or 43b, left and right two-dimensional images in which left and right sizes of the left side range and the right side range are changed.

The image processing section 42a generates, with a predetermined depth amount included in the inputted 3D video signal set as a reference depth amount, a 3D image signal of a depth amount suitable for the observing observer using the image parameter of the depth amount correction value inputted from the control section 45a side. Note that the reference depth amount means that left and right 2D images picked up by the image pickup sections 23a and 23b at the distance d in the 3D endoscope 4 are alternately displayed in the same display position. In other words, the case of the reference depth amount is equivalent to a state in which a 3D image signal generated from image pickup signals picked up by the image pickup sections 23a and 23b of the actually used 3D endoscope 4 is directly displayed on the 3D monitor.

As explained below, when a depth amount correction value serving as a correction value of a depth amount is inputted to the control section 45a from the 3D glasses, the control section 45a controls the image processing section 42a to correct the reference depth amount with the depth amount correction value. In this case, the display section 43a displays a 3D observation image obtained by correcting the reference depth amount by the depth amount correction value.

In this way, the image processing section 42a has a function of a depth-amount correcting section (or a depth-amount correction circuit) 47a functioning as depth-information correcting means for correcting a depth amount serving as depth information for giving a cubic effect (substantially determining a cubic effect). The image processing section 42a has a function of a color-tone correcting section (or a color-tone correction circuit) 48a functioning as color-tone correcting means for correcting a color tone of the 3D observation image displayed on the display section 43a.

Similarly, the second 3D monitor 8B includes a video input interface (a video input IF) 41b to which a 3D video signal is inputted, an image processing section (or an image processing circuit) 42b that performs image processing corresponding to image parameters such as a depth amount correction value on a 3D observation video (or a 3D observation image) displayed on a display section (or a display device) 43b from the inputted 3D video signal (image signal), the display section 43b that displays an image signal of the generated 3D observation image, an operation section (an operation device) or an operation input section (an operation input device) 44b that performs setting operation for image processing parameters of the image processing section 42b, a control section (or a control circuit) 45b that performs control of the image processing section 42b and the display section 43b, and an RF transmitting/receiving section (or an RF transmission/reception circuit) 46b that performs transmission and reception with the 3D glasses.

The RF transmitting/receiving section 46b includes a function of a scanning section (or a scanning circuit) 46ba that performs a scan for detecting the 3D glasses. The control section 45b controls the scanning section 46ba included in the RF transmitting/receiving section 46b to perform a scan for periodically detecting the 3D glasses. That is, the control section 45b controls the scanning section 46ba to periodically perform the scan for detecting the 3D glasses including the storing section. More specifically, after correcting, with a depth information correction value stored in the memory (provided in the 3D glasses) configuring the storing section, a 3D observation image displayed on the display section 43b of the 3D monitor 8B, the control section 45b controls the scanning section 46ba to periodically perform the scan for detecting the 3D glasses including the storing section.

As in the case of the first 3D monitor 8A, in the present embodiment, the 3D video signal (image signal) inputted to the second 3D monitor 8B is directly outputted to the display section 43b. A 3D image of the inputted 3D video signal can be displayed on the display section 43b as a 3D observation video (or a 3D observation image). However, the image processing section 42b inside the second 3D monitor 8B performs image processing for correcting, with an image parameter of a depth amount correction value, a depth amount serving as depth information for giving a cubic effect and substantially determining a degree of the cubic effect such that a 3D observation video (or a 3D observation image) having a cubic effect desired by the surgeon can be displayed. The surgeon observes (visually recognizes) the 3D observation video (or the 3D observation image), which is displayed on the display section 43b, as a 3D image using the 3D glasses.

The image processing section 42b generates, with a depth amount in the inputted 3D video signal set as a reference depth amount, a 3D image signal of a depth amount suitable for an observation using the image parameter of the depth amount inputted from the control section 45b side.

As explained below, when a depth amount correction value serving as a correction value of a depth amount is inputted to the control section 45b from the 3D glasses, the control section 45b controls the image processing section 42b to correct the reference depth amount with the depth amount correction value. In this case, the display section 43b displays a 3D observation image obtained by correcting the reference depth amount by the depth amount correction value.

In this way, the image processing section 42b has a function of a depth-amount correcting section (or a depth-amount correction circuit) 47b functioning as depth-information correcting means for correcting a depth amount serving as depth information for giving a cubic effect (substantially determining a cubic effect). The image processing section 42b has a function of a color-tone correcting section (or a color-tone correction circuit) 48b functioning as color-tone correcting means for correcting a color tone of the 3D observation image displayed on the display section 43b.

The 3D glasses 9A include left and right polarizing plates 51a and 51b respectively disposed to be located in front of the left and right eyes of the surgeon Da, an RF transmitting/ receiving section (or an RF transmission/reception circuit) 53a that performs transmission and reception with the monitor 8A or 8B by radio, and a memory 54a forming a storing section that stores a depth amount correction value and the like when the surgeon Da uses the 3D glasses 9A. Note that, in the left and right polarizing plates 51a and 51b, polarizing directions are set to transmit lights polarized in two directions orthogonal to each other. In the display section 43a or 43b, left and right images set to be alternately displayed and allow lights in the polarizing directions orthogonal to each other to pass can be respectively allowed to pass by the left and right polarizing plates 51a and 51b (the left image is allowed to pass by the polarizing plate 51a and the right image is allowed to pass by the polarizing plate 51b) and observed.

Similarly, the 3D glasses 9B include the left and right polarizing plates 51a and 51b respectively disposed to be located in front of the left and right eyes of the surgeon Db, an RF transmitting/receiving section (or an RF transmission/ reception circuit) 53b that performs transmission and reception with the monitor 8A or 8B by radio, and a memory 54b forming a storing section that stores a depth amount correction value and the like when the surgeon Db uses the 3D glasses 9B.

Similarly, the 3D glasses 9C include the left and right polarizing plates 51a and 51b respectively disposed to be located in front of the left and right eyes of the surgeon Dc, an RF transmitting/receiving section (or an RF transmission/ reception circuit) 53c that performs transmission and reception with the monitor 8A or 8B by radio, and a memory 54c forming a storing section that stores a depth amount correction value and the like when the surgeon Dc uses the 3D glasses 9C. Note that the RF transmitting/receiving sections 53a, 53b, and 53c have a function of data transmitting sections that mainly transmit image parameters such as depth amount correction values stored in the memories 54a, 54b, and 54c to the 3D monitor 8A or 8B.

Figure 4:
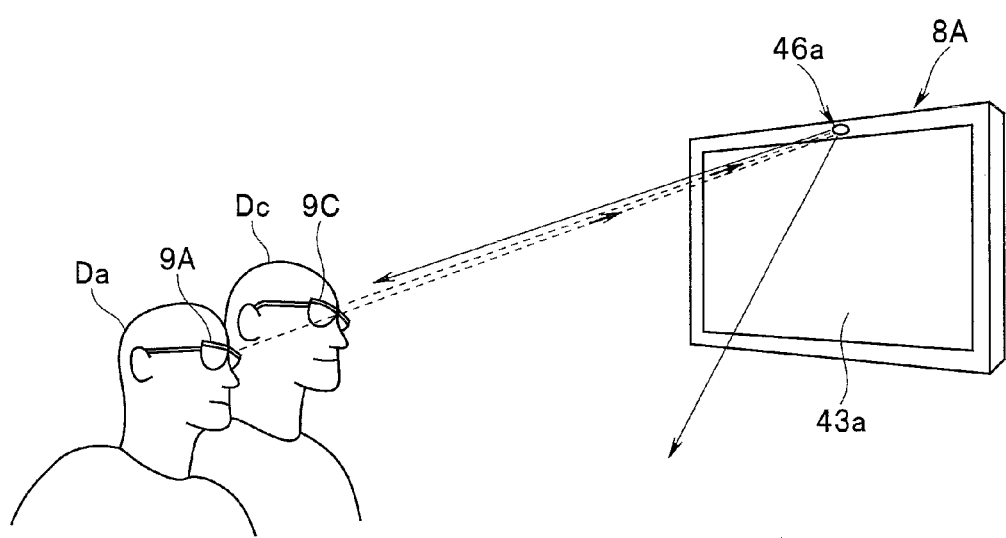
FIG. 4 is an explanatory diagram of a state in which a radio wave for detecting 3D glasses is transmitted toward an observation range, in which a display section is observable, by an RF transmitting/receiving section provided in a 3D monitor and the 3D glasses receiving the radio wave transmit a radio wave for reply to the 3D monitor.
Figure 5:
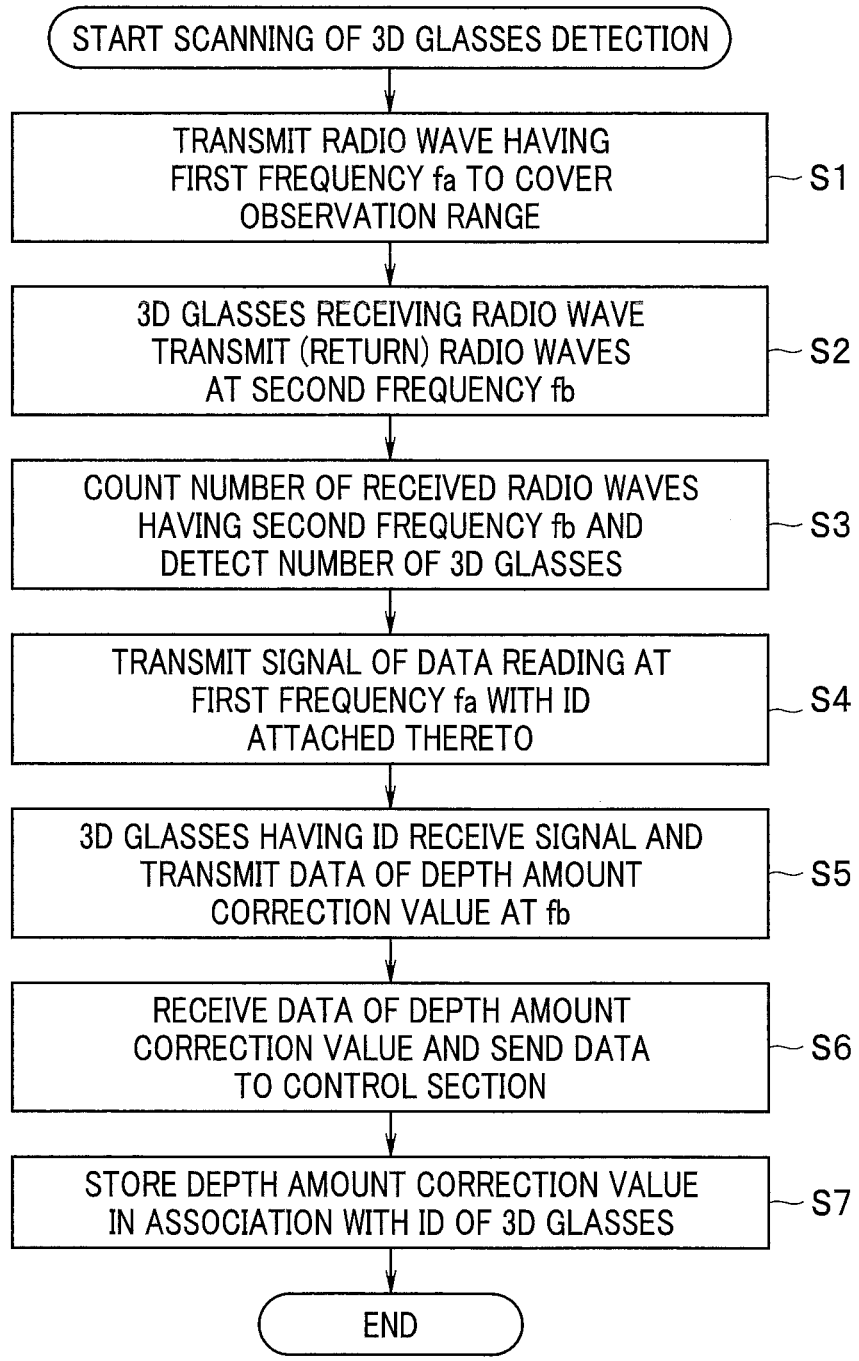
FIG. 5 is a flowchart showing a processing example corresponding to an operation shown in FIG. 4.

FIG. 4 shows a state in which (the scanning section 46aa of) the RF transmitting/receiving section 46a provided in the 3D monitor 8A transmits a radio wave for detecting the 3D glasses worn by the surgeon toward an observation range in which the display section 43a is observable and receives a radio wave transmitted from the 3D glasses that receive the radio wave. The case of FIG. 4 corresponds to the case of FIG. 1 or FIG. 2(A). The surgeon Da wearing the 3D glasses 9A and the surgeon Dc wearing the 3D glasses 9C are present within an observation range in which a 3D observation of the display section 43a of the 3D monitor 8A is possible. Note that, in the case of FIG. 1 or FIG. 2(A), the 3D glasses 9B of the surgeon Db are present in an observation range in which a 3D observation of the display section 43b of the 3D monitor 8B is possible. FIG. 5 shows a flowchart for operation explanation in the case of FIG. 4.

As shown in step S1, (the scanning section 46aa of) the RF transmitting/receiving section 46a of the 3D monitor 8A transmits a radio wave having directivity to travel straightforward at the first frequency fa as a scanning signal (a signal for detection) for detecting the 3D glasses to cover the observation range in which the 3D observation of the display section 43a is possible. When, for example, two surgeons Da and Dc are respectively wearing the 3D glasses 9A and 9C in the observation range as shown in FIG. 4, the RF transmitting/receiving sections 53a and 53c of the 3D glasses 9A and 9C respectively detect (catch) scanning signals of the first frequency fa.

The RF transmitting/receiving sections 53a and 53c are disposed in, for example, positions near upper surfaces of the polarizing plates 51a and 51b. The RF transmitting/ receiving sections 53a and 53c are also set to a characteristic having directivity to receive and transmit radio waves in a range of approximately several tens degrees centering on a direction nearly perpendicular to surfaces of the polarizing plates 51a and 51b. Therefore, for example, even if the surgeons Da and Dc respectively wear masks, the RF transmitting/receiving sections 53a and 53c can detect (catch) a scanning signal without being affected by the masks.

As shown in step S2, the RF transmitting and receiving sections 53a and 53c of the detected 3D glasses 9A and 9C perform processing for converting the first frequency fa of the detected radio wave into the second frequency fb and transmit a radio wave of the second frequency fb to the 3D monitor 8A side. In FIG. 4, a state in which the 3D glasses 9A and the like transmit the radio wave of the second frequency fb to the 3D monitor 8A side is indicated by dotted lines.

As shown in step S3, (the scanning section 46aa of) the RF transmitting/receiving section 46a of the 3D monitor 8A counts the number of radio waves of the second frequency fb to thereby detect the number of 3D glasses present within the observation range. (The scanning section 46aa of) The RF transmitting/receiving section 46a sends the detected number of 3D glasses to the control section 45a. The control section 45a stores information concerning the detected number of 3D glasses in a memory 49a on an inside.

In this way, after performing processing for detecting the number of the 3D glasses 9A and 9C present within the observation range, (the scanning section 46aa of) the RF transmitting/receiving section 46a shifts to processing of data reading in step S4 and subsequent steps (when a predetermined time elapses).

In step S4, the RF transmitting/receiving section 46a performs processing for identifying the detected number of 3D glasses and detects IDs serving as identification information. For example, the RF transmitting/receiving section 46a transmits a command for requesting transmission of IDs and the 3D glasses 9A and 9C receiving the command respectively return IDs, whereby the 3D monitor 8A detects the IDs of the 3D glasses 9A and 9C. After detecting the IDs, the RF transmitting/receiving section 46a transmits an instruction signal including a command for data reading at the first frequency fa with an ID serving as identification information attached to the instruction signal.

As shown in step S5, the 3D glasses having an ID coinciding with the transmitted ID receive, with the RF transmitting/receiving section, the instruction signal and decodes the command for the data reading. The 3D glasses read out a depth amount correction value stored in advance in the memory 54a on the inside and transmit the depth amount correction value at the second frequency fb. As shown in step S6, the RF transmitting/receiving section 46a of the 3D monitor 8A receives data of the transmitted depth amount correction value and sends the data to the control section 45a. As shown in step S7, the control section 45a stores the depth amount correction value in the memory 49a in association with the ID of the 3D glasses.

When a plurality of pairs of 3D glasses are detected, the same processing is repeated by changing IDs. The control section 45a stores depth amount correction values in the memory 49a by the number of the detected plurality of pairs of 3D glasses in association with IDs of the 3D glasses. The processing in FIG. 5 is performed in the respective 3D monitors 8A and 8B.

In this way, the scan for detecting 3D glasses and the processing of the data reading end. In FIGS. 4 and 5, the scan of the 3D glasses and the processing of the data reading from the 3D glasses detected by the scan are explained. On the other hand, FIG. 6 shows an explanatory diagram of an operation in which a surgeon using 3D glasses memorizes (stores) a depth amount correction amount suitable for the surgeon in a memory in the 3D glasses.

In an disposition state shown in FIG. 1 or FIG. 2(A), when the surgeon Da performs a surgical operation, before the surgical operation, the surgeon Da performs, on the 3D monitor 8A, operation of data writing for storing (memorizing) a depth amount correction value desired by the surgeon Da in the memory 54a of the 3D glasses 9A. The other surgeons Db and Dc perform the same operation.

Figure 6:
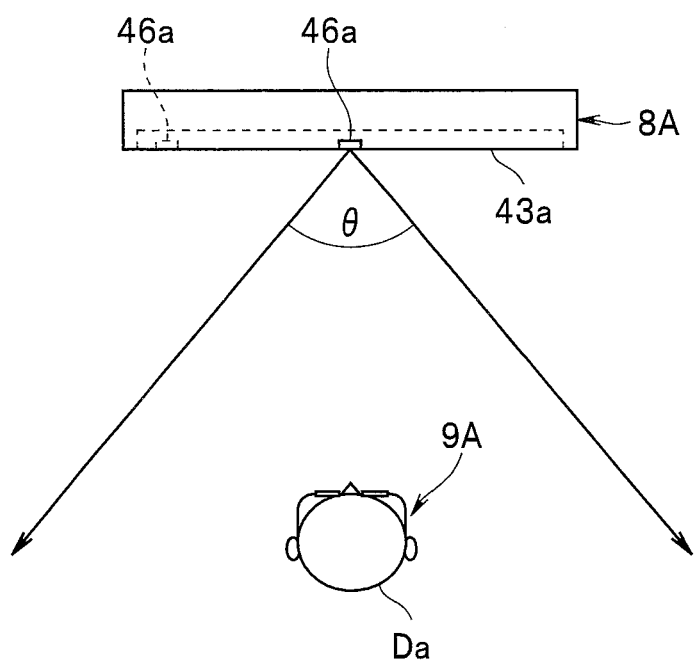
FIG. 6 is a diagram showing a state in which a depth amount correction value is set in a position where a surgeon wears the 3D glasses and observes the 3D monitor.
Figure 7:
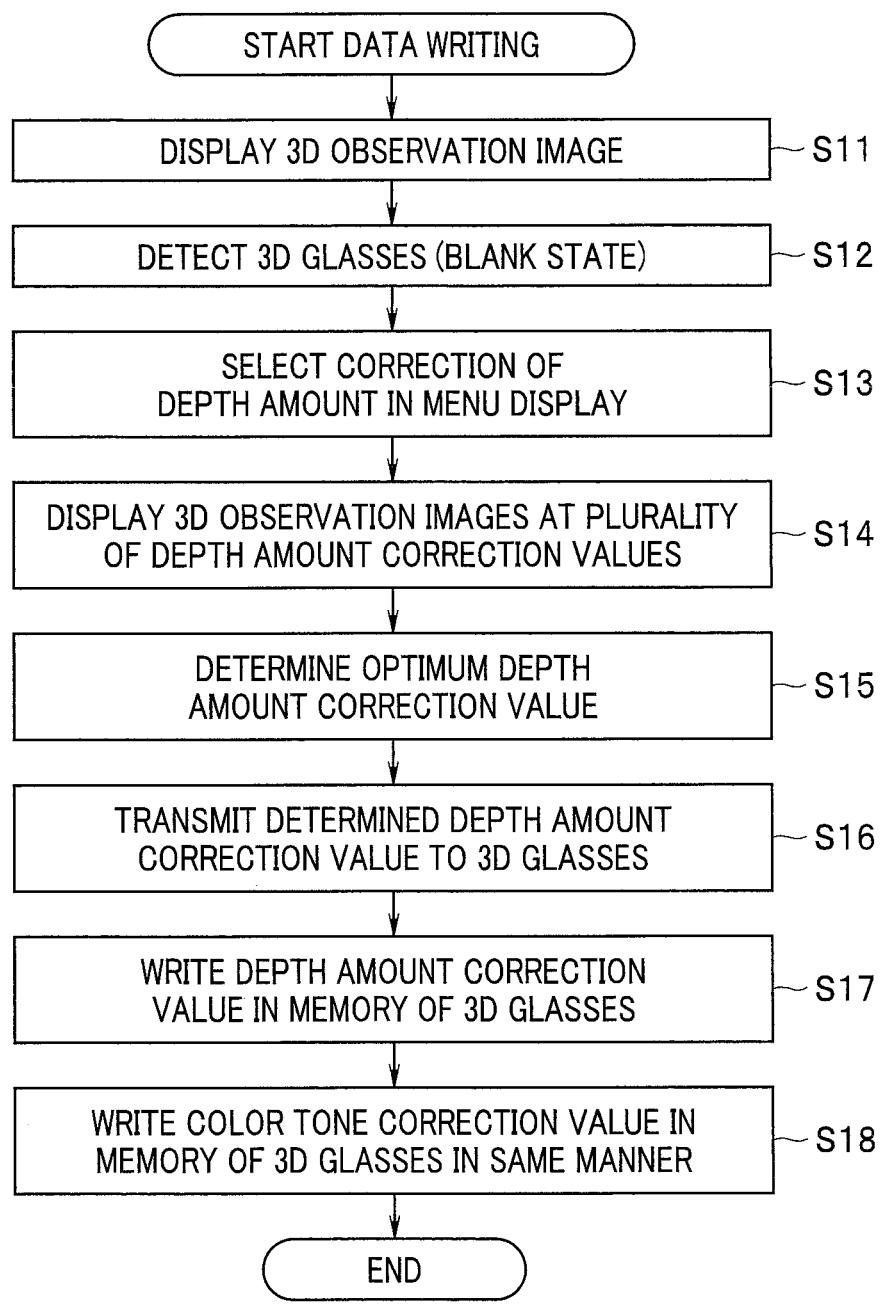
FIG. 7 is a flowchart showing a processing example in the case in which a depth amount correction value is written in the 3D glasses in the state of FIG. 6.

FIG. 6 extracts and shows, in a state of FIG. 1 or FIG. 2(A), (as an observation environment of the surgeon Da with respect to the 3D monitor 8A) a monitor disposition position where the 3D monitor 8A is actually disposed and a portion that is a standing position where the surgeon Da stands when the surgeon Da actually performs the surgical operation and is an observation position where the surgeon Da observes the 3D monitor 8A. FIG. 7 shows processing for writing data such as a depth amount correction value in the 3D glasses in the observation environment in FIG. 6.

In the observation environment shown in FIG. 6, the surgeon Da wears the 3D glasses 9A and observes the 3D monitor 8A. The 3D monitor 8A displays a 3D observation image with the reference depth amount as shown in step S11. In FIG. 6, a scan range of the scanning signal transmitted from the RF transmitting/receiving section 46a in FIG. 4 is indicated by θ. The scan range θ substantially corresponds to an observation range in which the surgeon is capable of performing a 3D observation.

As shown in step S12, the RF transmitting/receiving section 46a of the 3D monitor 8A detects the 3D glasses 9A. An ID is transmitted from the 3D glasses 9A and, since a state of the 3D glasses 9A is an initial state, and also data in a blank state (an empty state) in which data such as a depth amount correction value is not written in the memory 54a of the 3D glasses 9A is transmitted. The 3D monitor 8A identifies the ID transmitted from the 3D glasses 9A and identifies (detects) the blank state in which data is not written.

In the next step S13, the 3D monitor 8A displays a menu including a plurality of settable items on the 3D monitor 8A. The surgeon Da selects an item of depth amount correction from the menu. Note that, as the plurality of items, the menu includes setting of depth amount correction, a change of a depth amount correction value set before, setting (correction) of a color tone other than the depth amount correction, reading of data of the memory 54a, reset of the data of the memory 54a, and an end. Since the setting of the item selected from the plurality of items can be performed in this way, it is possible to change the depth amount correction value set before.

Note that, for the display of the menu, a program is set such that the processing for the data reading explained with reference to FIG. 5 is performed if operation of selection is not performed within a predetermined time (e.g., 5 or 6 seconds) set in advance. Therefore, for example, when a writing result of a depth amount correction value or the like set this time can be directly used the next time, the processing for the writing is unnecessary next time.

In the next step S14, the surgeon Da operates the operation section 44a of the 3D monitor 8A and, for example, causes the 3D monitor 8A to sequentially display 3D observation images with a plurality of depth amount correction values. The control section 45a sequentially sends, according to the operation from the operation section 44a, the plurality of depth amount correction values to the image processing section 42a. The image processing section 42a sequentially outputs image signals of the 3D observation images having the plurality of depth amount correction values to the display section 43a. The display section 43a sequentially displays the 3D observation images having the plurality of depth amount correction values. As shown in step S15, the surgeon Da observes the sequentially displayed 3D observation images, selects, with the operation section 44a, a 3D observation image considered to be best or optimum, and determines an optimum depth amount correction value corresponding to the selection.

FIG. 8 shows an explanatory diagram of a relation among the reference depth amount, a depth amount correction value for correction with respect to the reference depth amount, and left and right 2D images for generating a 3D observation image corrected with the depth amount correction value.

As shown in FIG. 8(A), optical images of an object O such as a diseased part are formed on image pickup surfaces 22ap and 22bp of the CCDs 22a and 22b of the image pickup sections 23a and 23b separated by the distance d in the 3D endoscope 4 and photoelectrically converted (picked up). In object portions at a distance Lo from the object lenses 21a and 21b, optical images in a common range are respectively formed. However, left and right ranges Ra and Rb indicated by hatching are respectively ranges in which image pickup is performed by one image pickup section but is not performed by the other image pickup section. Therefore, for example, in an object portion at a distance L1 indicated by a dotted line, optical image portions Pa and Pb picked up by only one image pickup section each other occur on the image pickup surfaces 22ap and 22bp of the CCDs 22a and 22b. More specifically, the optical image portion Pa corresponds to an optical image portion obtained by picking up an image of a left side portion of the object and the optical image portion Pb corresponds to an optical image portion obtained by picking up a right side portion of the object. Note that optical image portions picked up in common are indicated by Pc. Left and right optical images are represented as Pl(=Pc+Pa) and Pr(=Pc+Pb).

In the present embodiment, as shown in FIG. 8(B) showing a part of FIG. 8(A) in enlargement, the image pickup surfaces 22ap and 22bp include image pickup regions (effective image pickup regions) Re used in actual display areas of 3D observation images on the display sections 43a and 43b and outer side image pickup regions Ro provided on both outer sides of the effective image pickup region Re. FIG. 8(B) enlarges vicinities of the image pickup surfaces 22ap and 22bp in FIG. 8(A) and shows the effective image pickup regions Re and the outer side image pickup regions Ro.

When left and right 2D images obtained by directly displaying optical images Pl and Pr picked up by the effective image pickup regions Re of the CCDs 22a and 22b respectively on the display section 43a or 43b of the 3D monitor 8A or 8B are represented as Il and Ir (see FIG. 8(C)), the left and right 2D images Il and Ir are images or picked-up images equivalent to the left and right optical images Pl and Pr formed in the effective image pickup regions Re on the image pickup surfaces 22ap and 22bp of the CCDs 22a and 22b.

FIG. 8(c) shows, separately in upper and lower parts, for example, a case in which the left 2D image Il (equivalent to the left optical image Pl formed on the image pickup surface 22*ap*) is displayed and a case in which the right 2D image Ir (equivalent to the right optical image Pr formed on the image pickup surface 22*bp*) is displayed on a display surface 43*a*' of the display section 43*a*. Note that the same applies to the display surface of the display section 43*b*.

The 2D image Il includes a common image portion Ic and an image portion (i.e., a non-common image portion) Ia present only in the 2D image Il on a left side and obtained by picking up an image of a left side portion of an object. Similarly, the 2D image Ir includes the common image portion Ic and an image portion (i.e., a non-common image portion) Ib present only in the 2D image Ir on the right side and obtained by picking up an image of a right side portion of the object.

Note that, in FIG. 8(C), in order to clarify that the 2D images Il and Ir respectively correspond to the optical images Pl and Pr, the 2D images Il and Ir are shown as Il(Pl) and Ir(Pr). Ic, Ia, and Ib are also shown as Ic(Pc), Ia(Pa), and Ib(Pb). When the distance d in FIG. 8(A) is, for example, increased, the hatched ranges Ra and Rb increase, for example, the optical image portions Pa and Pb in 2D images Pl and Pr in FIG. 8(B) respectively increase, and, when the 2D images Il and Ir are displayed as a 3D observation image on the display sections 43*a* and 43*b*, a cubic effect in observation by the surgeon further increases. Conversely, when the distance d is reduced, the hatched regions Ra and Rb decrease, the optical image portions Pa and Pb in 2D images Pl and Pr in FIG. 8(B) respectively decrease, and when the 2D images Il and Ir are displayed as 3D observation images on the display sections 43*a* and 43*b*, a cubic effect in the observation by the surgeon decreases.

Therefore, when the image pickup sections 23*a* and 23*b* having the predetermined distance d are used, by changing sizes in the left-right direction of the optical image portions Pa and Pb (the left side portion Pa of the object and the right side portion Pb of the object) or the non-common image portions Ia and Ib picked up by only one image pickup section and generating a 3D observation image, it is considered possible to substantially change magnitude of a cubic effect sensed by the surgeon when the surgeon observes the 3D observation image.

In this way, in this specification, the depth-amount correcting sections 47*a* and 47*b* functioning as depth-amount correcting means are provided that changes a cubic effect in the case of observation by the surgeon by adjusting, as a depth amount correction value, magnitude of a size in the left-right direction of the non-common image portions Ia and Ib (the left side image pickup range or the left side range Ia and the right side image pickup range or the right side range Ib). Note that, since a display area where the 3D observation image is displayed in the display section is fixed, when the magnitude of the size in the left-right direction of the non-common image portions Ia and Ib is changed, a size of the common image portions Ic is also changed according to the change.

As explained above, in the CCDs 22*a* and 22*b*, the outer side image pickup regions Ro are provided on both outer sides in the left-right direction of the effective image pickup regions Re. Therefore, even when the magnitude of the size in the left-right direction of the non-common image portions Ia and Ib is changed as the depth amount correction value, by using images of the outer side image pickup regions Ro, it is possible to prepare left and right 2D images to be displayed as a 3D observation image without losing a part of the images.

For example, the optical image Pl in the state shown in FIG. 8(B) includes the common optical image portion Pc and the non-common optical image portion Pa. However, in order to maximize a depth amount correction value to increase a cubic effect, it is possible to set a non-common optical image portion as Pa+Ro and set a common optical image portion as Pc−Ro. The case of the optical images is explained above. However, the explanation can also be applied to the case of 2D images based on picked-up images photoelectrically converted from the optical images.

FIG. 8(D) shows, for example, with a depth amount correction value represented as h, sizes of the common image portions Ic and the non-common image portions Ia and Ib of left and right 2D images displayed as 3D observation images in the cases in which the depth amount correction value h is three values of −i (represented as h(−i)), h(0), and h(+i).

Note that the depth amount correction value h(0) corresponds to the reference depth amount, the depth amount correction value h(−i) corresponds to a depth amount reduced by an i stage from the depth amount correction value h(0), and the depth amount correction value h(+i) corresponds to a depth amount increased by the i stage from the depth amount correction value h(0). At the depth amount correction value h(−i), compared with the depth amount correction value h(0), the size in the left-right direction of the non-common image portions Ia and Ib decreases by the i stage. Conversely, at the depth amount correction value h(+i), compared with the depth amount correction value h(0), the size in the left-right direction of the non-common image portions Ia and Ib increases by the i stage.

The surgeon Da observes the 3D observation images schematically shown in FIG. 8(D), selects, as explained above, from the operation section 44*a*, a 3D observation image in the case of a depth amount correction value considered to be optimum as shown in step S15 in FIG. 7, and determines the depth amount correction value corresponding to the selection.

In the next step S16, the control section 45*a* of the 3D monitor 8A controls the RF transmitting/receiving section 46*a* to transmit the determined depth amount correction value to the 3D glasses 9A. In step S17, the 3D glasses 9A receive the transmitted depth amount correction value and write data of the depth amount correction value in the memory 54*a* in the 3D glasses 9A. When the writing of the data of the depth amount correction value ends, the RF transmitting/receiving section 53*a* of the 3D glasses 9A transmits a signal of the end of the writing to the 3D monitor 8A.

When receiving the signal, the 3D monitor 8A displays the menu again. The surgeon Da ends the processing for writing the depth amount correction value in the memory 54*a*. When the surgeon Da further desires to correct a color tone of the 3D observation image, the surgeon Da selects setting (correction) of the color tone from the menu.

The surgeon Da may read the depth amount correction value as a correction value of the color tone to perform the processing in steps S14 to S16. After performing the processing for writing data of the determined color tone correction value in the memory 54*a* in the 3D glasses 9A, the surgeon Da may end the processing in FIG. 7. The memory 54*a* in the 3D glasses 9A has a function of a depth-amount-correction-value storing section (or a depth-amount-correction-value storing device) 55*a* that stores the depth amount correction value determined by the surgeon Da and a function of a color-tone-correction-value storing section (or a color-tone-correction-value storing device) 56*a* that stores the color tone correction value determined by the surgeon Da.

Figure 9A:
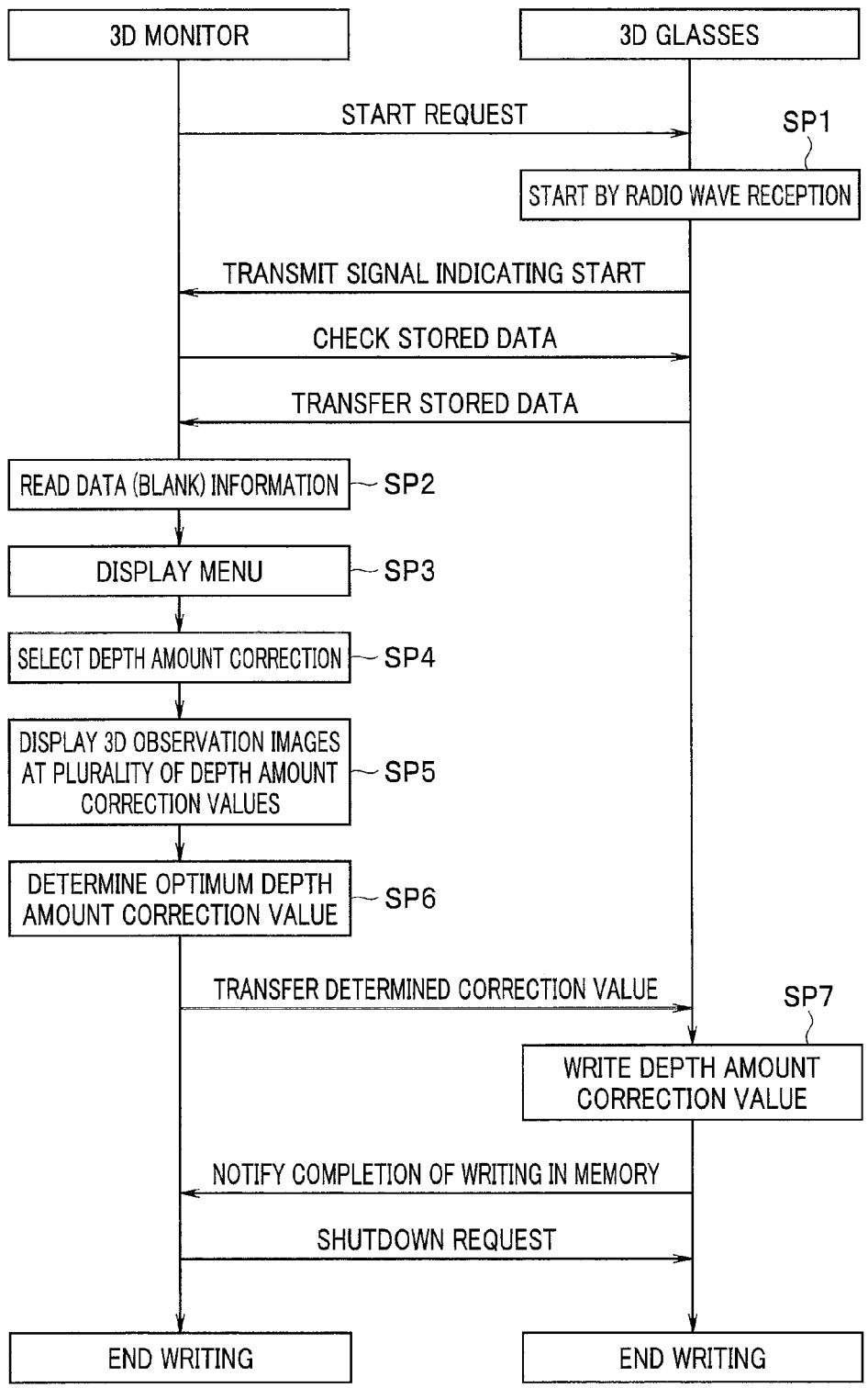
FIG. 9A is a diagram showing a processing sequence in the case in which data writing is performed in the 3D glasses.

FIG. 9A shows a processing sequence for performing writing of data between the 3D monitor 8A and the 3D glasses 9A in FIG. 7 when data such as a depth amount correction value in the memory 54a of the 3D glasses 9A is blank. An ordinate in FIG. 9A indicates elapse of time. The 3D monitor 8A transmits, from the RF transmitting/receiving section 46a, as a radio wave, a start request for starting the 3D glasses 9A to the 3D glasses 9A. The 3D glasses 9A receive the radio wave and start (processing SP1). After the start, the 3D glasses 9A return a signal indicating the start to the 3D monitor 8A.

When receiving the returned signal, the 3D monitor 8A transmits a signal of a data request for checking data stored in the memory 54a in the 3D glasses 9A to the 3D glasses 9A. The 3D glasses 9A transfer the data stored in the memory 54a to the 3D monitor 8A in response to the data request. In a first state, since the memory 54a of the 3D glasses 9A is in a blank state, the 3D glasses 9A transfer blank data in which a data portion is blank.

The 3D monitor 8A reads the transferred (blank) data (processing SP2) and grasps that the memory 54a is in the blank state in which data is not written. Note that, for example, in reading the (blank) data, the 3D monitor 8A identifies an ID serving as identification information of the 3D glasses 9A.

Subsequently, the 3D monitor 8A displays a menu (processing SP3). When the menu is displayed, the surgeon operates the operation section 44a to perform selection of depth amount correction (selection for correcting a depth amount) (processing SP4).

The 3D monitor 8A sequentially performs display of 3D observation images with a plurality of depth amount correction values (processing SP5). The surgeon observes the 3D observation images and determines, with operation of the operation section 44a, a depth amount correction value in the case of a 3D observation image considered to be optimum (processing SP6). Receiving the operation, the 3D monitor 8A transfers the determined depth amount correction value to the 3D glasses 9A.

The 3D glasses 9A write (store) the transferred depth amount correction value in the memory 54a (processing SP7). After performing the writing, the 3D glasses 9A notify the 3D monitor 8A that the writing is completed. Receiving the notification, the 3D monitor 8A transmits a shutdown request for requesting shutdown to the 3D glasses 9A. The 3D glasses 9A shut down and the processing in FIG. 9 ends. In this way, the surgeon Da can write a depth amount correction value desired by the surgeon Da in the memory 54a of the 3D glasses 9A. Note that, as explained above, a color tone correction value can be further written in the memory 54a of the 3D glasses 9A. The above explanation is explanation of an operation for writing a depth amount correction value when the surgeon Da observes the 3D monitor 8A in FIG. 1 or FIG. 2(A).

Figure 9B:
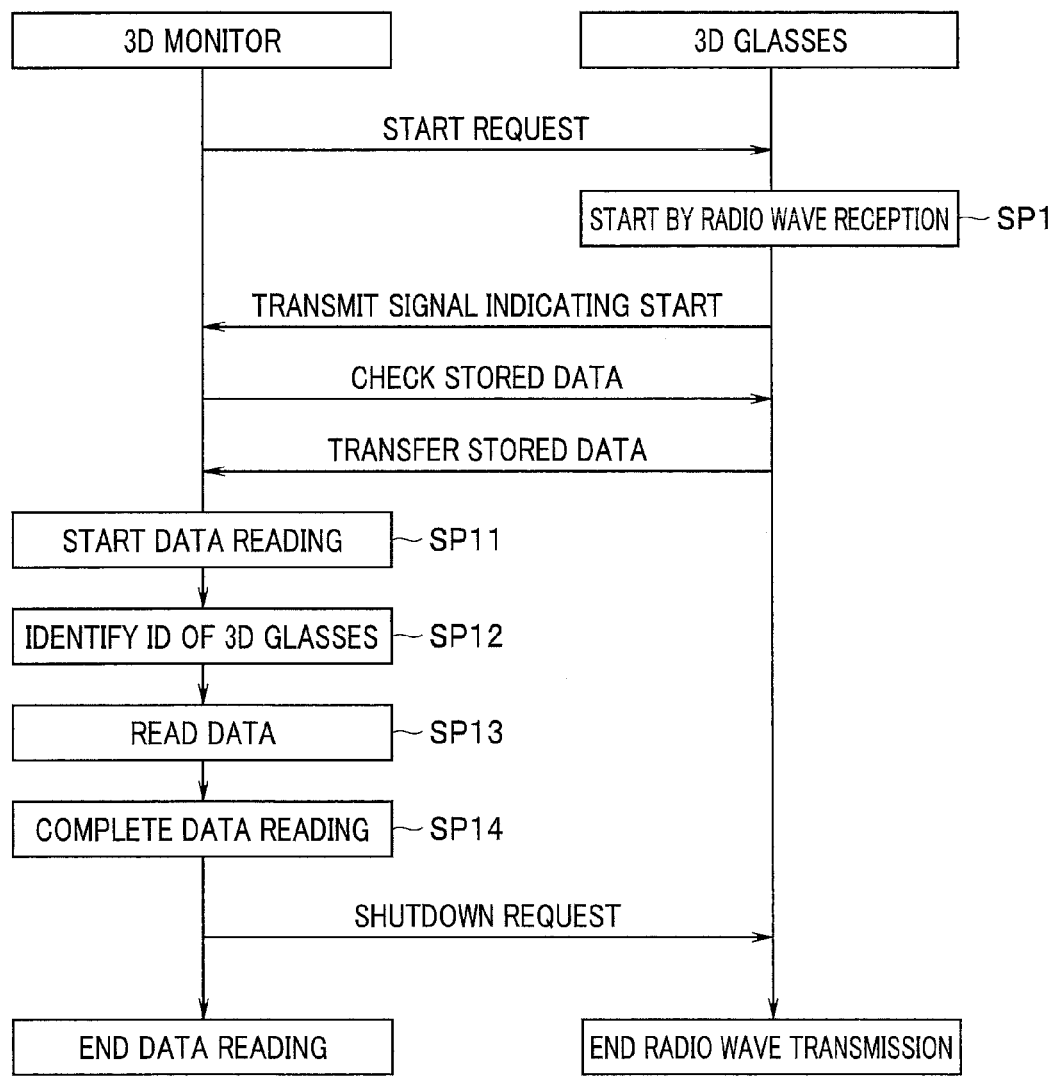
FIG. 9B is a diagram showing a processing sequence in the case in which data reading is performed from the 3D glasses in which data is written.

After the data is written in the 3D glasses 9A as shown in FIG. 9A, processing for passing the data in the 3D glasses 9A to the 3D monitor 8A is as shown in FIG. 9B.

Processing from a start request to transfer of stored data in FIG. 9B is the same as the processing in FIG. 9A. Therefore, explanation of the processing is omitted. The 3D monitor 8A receives the transfer of the data. Since the transferred data is not blank, the 3D monitor 8A starts data reading (processing SP11). The 3D monitor 8A identifies an ID of the 3D glasses 9A (processing in SP12). The 3D monitor 8A performs reading of data of the 3D glasses 9A (processing SP13). The 3D monitor 8A completes the reading of the data of the 3D glasses 9A (processing SP14). After the reading of the data is completed, the 3D monitor 8A sends a shutdown request to the 3D glasses 9A. The 3D glasses 9A end the radio wave transmission. The 3D monitor 8A ends the processing of the data reading and ends the processing in FIG. 9B.

Note that, in the processing sequence in FIG. 9B, for example, when the 3D monitor 8A detects only one pair of 3D glasses 9A, after the reading of the data is completed, the 3D monitor 8A changes to a setting state in which the 3D monitor 8A performs image processing corresponding to the read data such as the depth amount correction value.

Figure 11:
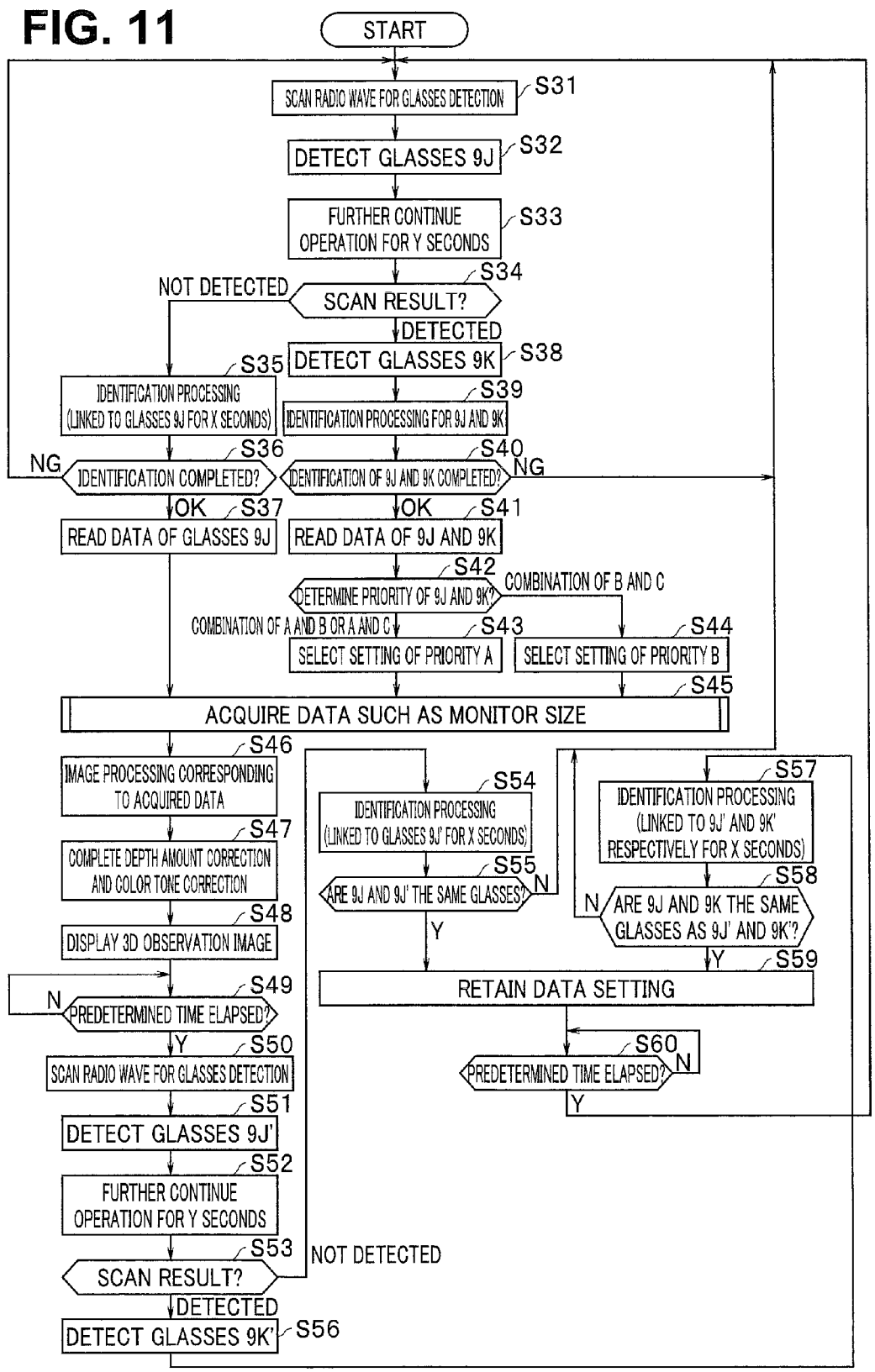
FIG. 11 is a flowchart showing a processing example of a representative operation in the first embodiment.

On the other hand, when the 3D monitor 8A detects a plurality of pieces of 3D glasses, the 3D monitor 8A temporarily stores the data of the respective pairs of 3D glasses acquired in the processing sequence in FIG. 9B in, for example, the memory 49a in the control section 45a and changes to a setting state in which the 3D monitor 8A performs, taking into account surgeon priority (also referred to as priority or priority order), image processing corresponding to data read from 3D glasses worn by a surgeon having high priority (see FIG. 11 referred to below).

As shown in FIG. 2(B), when the surgeon Da changes a surgical operation position during a surgical operation and changes a 3D monitor according to the change of the position, in the position in FIG. 2(B), the surgeon Da performs the processing in FIG. 7 in a state in which the 3D monitor 8B is observed.

In FIG. 9A, when a depth amount correction value is determined and the determined depth amount correction value is stored in the memory 54a in the 3D glasses 9A, it is desirable to store information concerning monitor sizes (display sizes) of the 3D monitors 8A and 8B as well. Information concerning whether the 3D monitors 8A and 8B are used in a color mode or used in a monochrome mode may be stored.

Further, when a situation in which surgeons other than one surgeon Da, that is, a plurality of surgeons simultaneously observe one 3D monitor 8A or 8B occurs during a surgical operation, information concerning priority order or information concerning priority indicating, when the same 3D monitor is simultaneously observed, for 3D glasses of which surgeon the 3D monitor is preferentially set is desirably stored in memories of 3D glasses worn (used) by the plurality of surgeons. As explained below, in such a case, the 3D monitor is set in a state in which the 3D monitor performs display of a 3D observation image prioritizing data of 3D glasses worn by a surgeon having highest priority or priority order.

In FIG. 6 to FIG. 9B, the operation performed in the case of the surgeon Da and the 3D glasses 9A worn by the surgeon Da is explained. However, the operation is performed in the same manner in the surgeons Db and Dc.

In this way, for example, data shown in FIG. 10 is stored in 3D glasses 9J (j=A, B, and C) in association with IDs. FIG. 10 is, for example, data in the case of the surgeon Db. In association with IDs of 3D glasses, data of a monitor size, surgeon priority, a depth amount correction value, a color tone correction value, setting of presence or absence of a color mode of 3D monitors (in the case of FIGS. 1, 8A and 8B) that the surgeon Db observes wearing the 3D glasses are written. Note that, even in the case of a blank state in which data such as a depth amount correction value is not written, IDs serving as identification information are written in (ROM memories, etc. of) the respective pairs of 3D glasses in advance and given to the respective pairs of 3D glasses.

The surgeon priority is priority of order of A, B, C, D, . . . . The color tone correction value indicates a value to be corrected from a hue, chroma, and brightness of standard setting values. A − symbol denotes that setting of correction is not performed, ○ denotes the setting of the color mode, and × denotes the setting of a monochrome mode. In a setting example of the color tone correction value in FIG. 10, the setting of correction is not performed for the hue and the brightness from the standard setting value. Only the chroma is set to be slightly large.

Note that, in the example shown in FIG. 10, the depth amount correction value is defined as, for example, a size in the left-right direction of the image portions Ia and Ib shown in FIG. 8(D) in the case of a predetermined monitor size (display size). Therefore, as the monitor size is larger, the depth amount correction value is set larger. For example, a depth amount correction value of +3 in FIG. 10 is equivalent to h(+3) when the depth amount correction value h explained with reference to FIG. 8(D) is used. The depth amount correction value is not limited to such a definition and may be defined by a relative ratio of the image portions Ia and Ib to the images Il and Ir. In FIG. 10, besides the case of the two monitor sizes, data in the case of three monitor sizes are shown to correspond to a case in which one monitor size is changed.

In the present embodiment, in the memories on the respective pairs of 3D glasses side to which the IDs are respectively given, image parameters such as depth amount correction values desired by surgeons using the 3D glasses are stored (saved) (in association with the IDs). Therefore, it is unnecessary to save image parameters such as depth amount correction values (in association with the IDs) on the 3D monitor side functioning as display apparatuses. Data management is almost unnecessary or facilitated. The 3D monitor functioning as the display apparatus can display, with a simple configuration, a 3D observation image with image parameters such as a depth amount correction value desired by the surgeon.

Note that, in this way, it is unnecessary to save the image parameters such as the depth amount correction value on the 3D monitor side. However, the image parameters may be saved until the 3D monitor is used next time (in other words, it is unnecessary to erase the image parameters when an endoscopic test ends once) or the image parameters may be reset every time the endoscopic test is performed once.

The three-dimensional image system 1 in the present embodiment includes the 3D mixer 7 configuring an image generating apparatus that generates an image signal of a three-dimensional image for performing a three-dimensional observation, the 3D monitors 8A and 8B functioning as monitors that display, as an image for three-dimensional observation, the image signal generated by the image generating apparatus, the 3D glasses 9A, 9B, and 9C configuring glasses for three-dimensional observation for observing, as a three-dimensional image, the image for three-dimensional observation displayed on display sections of the monitors, memories 54a, 54b, and 54c provided in the glasses for three-dimensional observation and configuring a storing section that stores a depth information correction value for correcting depth information for giving a cubic effect of the image for three-dimensional observation displayed on the display section, the RF transmitting/receiving sections 46a and 46b including the scanning sections 46aa and 46ba that perform a scan for detecting the glasses for three-dimensional observation including the storing section in order to read information stored in the storing section, and the control sections 45a and 45b that perform control to set, according to scanning results of the scanning sections 46aa and 46ba, in the monitor, the depth information correction value stored in the storing section.

An operation in the present embodiment is explained. When the plurality of surgeons Da, Db, and Dc perform a surgical operation as shown in FIG. 1, the surgeons Da, Db, and Dc respectively wear the 3D glasses 9A, 9B, and 9C and perform work for writing depth amount correction values and the like as shown in FIG. 6 to FIG. 9A and the like. After the work for writing the depth amount correction values and the like desired by the surgeons Da, Db, and Dc in the respective pairs of 3D glasses 9A, 9B, and 9C ends in this way, the surgeons Da, Db, and Dc stand in positions for surgery shown in FIG. 1 or FIG. 2(A) and start a surgical operation. Representative processing of the three-dimensional image system 1 in the present embodiment during the start of the surgical operation is as shown in FIG. 11.

In FIG. 11, the 3D monitor 8A or 8B configuring the three-dimensional image system 1 periodically scans, from the RF transmitting/receiving section 46a or 46b, the 3D glasses 9A, 9B, and 9C worn by the surgeons acting as the observers who observe the 3D monitor 8A or 8B, automatically changes, according to a scanning result, a depth amount correction value and the like displayed on the 3D monitor 8A or 8B, and supports, even when a surgeon changes a position for surgery during a surgical operation, the surgeon to smoothly proceed with the surgical operation.

After starting a scan operation in FIG. 11, in first step S31, the 3D monitor 8A or 8B scans a radio wave for 3D glasses detection as shown in FIG. 4 from the RF transmitting/receiving section 46a or 46b. When the 3D glasses 9J are present in a scan range, the 3D monitor 8A or 8B detects the 3D glasses 9J (step S32). Note that, in FIG. 11, 3D glasses are simply referred to as glasses.

After the 3D glasses 9J are detected, the RF transmitting/receiving section 46a of the 3D monitor 8A or the RF transmitting/receiving section 46b of the 3D monitor 8B further continues the scan for 3D glasses detection for a predetermined time (e.g., for Y seconds) (step S33). Thereafter, in step S34, the RF transmitting/receiving section 46a or the RF transmitting/receiving section 46b performs determination of a result of the scan in step S33.

When further 3D glasses 9K are not detected as a result the determination in step S34, in step S35, the RF transmitting/receiving section 46a or the RF transmitting/receiving section 46b performs identification processing for the 3D glasses 9J detected in step S32 for, for example, X seconds. As the identification processing, the RF transmitting/receiving section 46a or the RF transmitting/receiving section 46b is set in a communication state (referred to as link state) for performing communication with the 3D glasses 9J and identifies an ID of the 3D glasses 9J. In step S36 after the identification processing in step S35, the 3D monitor 8A or 8B determines whether the identification processing has been able to be normally completed.

When the identification processing in step S36 has been able to be normally completed, in the next step S37, the 3D monitor 8A or 8B performs processing for reading data in a memory in the 3D glasses 9J and thereafter proceeds to processing for acquisition of data such as a monitor size in step S45. On the other hand, when the identification processing in step S36 has not been able to be normally completed, the 3D monitor 8A or 8B returns to the processing in the first step S31.

When further 3D glasses (other than the 3D glasses 9J) are detected in the processing in step S34, processing for 3D glasses 9K detection in step S38 is performed. When the 3D glasses 9K are detected as shown in step S38, in the next step S39, the 3D monitor 8A or 8B performs identification processing for the 3D glasses 9J and 9K for, for example, X seconds or a double of X seconds.

As the identification processing, the 3D monitor 8A or 8B is set in the link state for performing communication respectively with the 3D glasses 9J and 9K and performs processing for identifying IDs of the 3D glasses 9J and 9K. In step S40 after the identification processing in step S39, the 3D monitor 8A or 8B determines whether the identification processing has been able to be normally completed.

When the identification processing in step S40 has not been able to be normally completed, the 3D monitor 8A or 8B returns to the processing in step S31. On the other hand, when the identification processing in step S40 has been able to be normally completed, in the next step S41, after performing processing for reading data in memories in the 3D glasses 9J and 9K, the 3D monitor 8A or 8B extracts data of priority and performs processing for priority determination in step S42.

According to the processing for the priority determination in step S42, in the case of the combination in FIG. 1 or FIG. 2(A), the 3D monitor 8A determines (recognizes) that priority A of the 3D glasses 9A worn by the surgeon Da is higher than priority C of the 3D glasses 9C worn by the surgeon Dc. In step S43, the 3D monitor 8A selects setting of the priority A. In other words, the 3D monitor 8A more preferentially selects data of image parameters such as a depth amount correction value, for which priority is set high, than data of priority B and the priority C and selects setting of a 3D observation image. Note that, although not shown in FIG. 2(A) and FIG. 2(B), for example, when the 3D monitor 8A detects a combination of the 3D glasses 9A worn by the surgeon Da and the 3D glasses 9B worn by the surgeon Db, in step S43, the 3D monitor 8A selects setting of the priority A.

On the other hand, in the case of the 3D monitor 8B in FIG. 2(B), the 3D monitor 8B determines (recognizes) that the 3D glasses 9B worn by the surgeon Db have higher priority than the 3D glasses 8C worn by the surgeon Dc. In step S44, the 3D monitor 8A selects setting of the priority B. Note that, in the case of the 3D monitor 8B in FIG. 2(A) or FIG. 2(B), the processing of priority is not performed because only one surgeon Db or Da observes the 3D monitor 8B.

Figure 12:
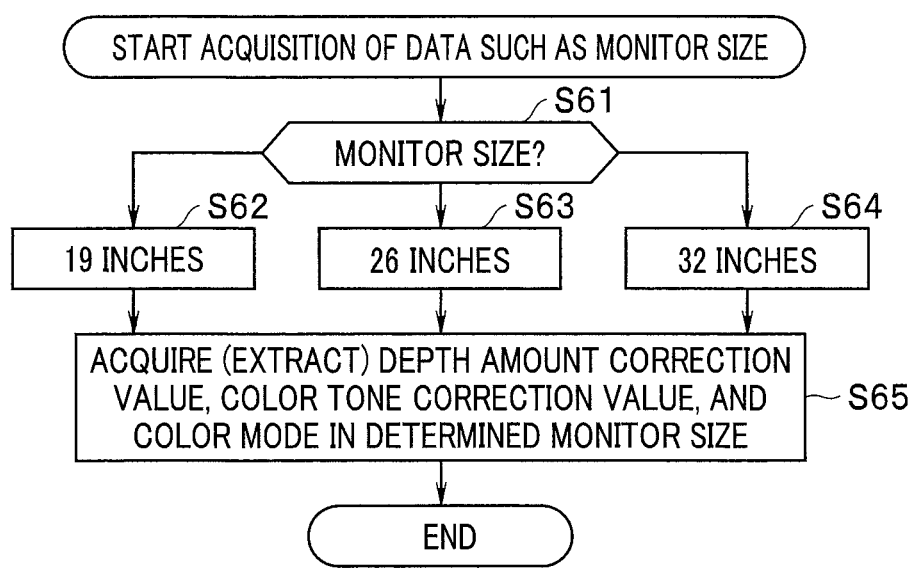
FIG. 12 is a flowchart showing content of processing for acquisition of data such as a monitor size.

After performing the processing in step S43 or step S44, the 3D monitor 8A performs processing for acquisition of data such as a monitor size in step S45. In FIG. 12, details of the processing for acquisition of data such as a monitor size are explained.

As shown in FIG. 12, when the processing for acquisition of data such as a monitor size is started, in step S61, in the case of the detected 3D classes 9J or in the case of the 3D glasses 9J and 9K, the 3D monitor 8A or 8B performs processing for determining a monitor size in data read out from an incorporated memory. In an example shown in FIG. 12, according to the monitor sizes shown in FIG. 10, the 3D monitor 8A or 8B determines three monitor sizes of 19 inches, 26 inches, and 32 inches as shown in steps S62, S63, and S64.

In step S65 after the determination of the respective monitor sizes in steps S62, S63, and S64, in the case of the relevant monitor size, the 3D monitor 8A or 8B acquires (extracts) data of a depth amount correction value, a color tone adjustment value, and a color mode in the one pair of 3D glasses 9J read in step S37 or 3D glasses having high priority in the two pairs of 3D glasses 9J and 9K read in step S41 and stores the data in, for example, the memory 49a or 49b in the control section 45a or 45b. In this way, the 3D monitor 8A or 8B ends the processing in FIG. 12 and proceeds to the processing in step S46 in FIG. 11.

In step S46, (the control section 45a or 45b of) the 3D monitor 8A or 8B controls image processing by the image processing section 42a or 42b in the setting target 3D monitor 8A or 8B according to the data of the depth amount correction value, the color tone correction value, and the color mode acquired from the 3D glasses. For example, the depth-amount correcting section 47a or 47b performs depth amount correction corresponding to the depth amount correction value. The color-tone correcting section 48a or 48b performs color tone correction corresponding to the color tone adjustment value. As shown in the next step S47, the 3D monitor 8A or 8B completes the depth amount correction, the color tone correction, and the like. As shown in step S48, the 3D monitor 8A or 8B displays a 3D observation image in a setting state of a completed state.

Therefore, in the case of one surgeon, the surgeon observing the 3D monitor 8A or 8B can observe the 3D observation image in a display form conforming to data stored in advance in a memory of 3D glasses worn by the surgeon. In the case of two surgeons, the surgeon can observe the 3D observation image in a display form conforming to data stored in advance in a memory of 3D glasses worn by a surgeon having high priority.

In the next step S49, the 3D monitor 8A or 8B waits until a predetermined time elapses from time when the processing in step S31 is started. When the predetermined time elapses, in the next step S50, as in the case of step S31, the 3D monitor 8A or 8B performs a scan to cover an observation range of a radio wave for 3D glasses detection and detects 3D glasses. According to the scan, as shown in step S51, the 3D monitor 8A or 8B detects 3D glasses 9J'.

In step S52, as in the case of steps S33, the 3D monitor 8A or 8B further continuously performs the scan for Y seconds. Thereafter, in step S53, as in the case of step S34, according to a scanning result, the 3D monitor 8A or 8B determines whether glasses are further detected. In the case of a determination result indicating that glasses are not detected, in step S54, as in the case of step S35, the 3D monitor 8A or 8B performs identification processing for the 3D glasses 9J'.

After performing the identification processing, in step S55, the 3D monitor 8A or 8B determines, according to IDs, whether the 3D glasses 9J detected and identified before and the 3D glasses 9J' detected and identified this time are the same 3D glasses. In the case of a determination result indicating that the 3D glasses 9J and 9J' are not the same 3D glasses (a determination result indicating that the IDs do not coincide with each other), the 3D monitor 8A or 8B returns to the processing in the first step S31. Processing (substantially the same as the processing for the 3D glasses 9J explained above) is performed on the 3D glasses 9J'. When one pair of 3D glasses 9J' is detected, a 3D observation image of the observation target 3D monitor is corrected according to a depth information correction value and the like stored in a storing section (a memory) of the 3D glasses 9J'. In other words, when an observer observing the same 3D monitor temporally changes (when one first observer is replaced by one second observer), according to a depth information correction value and the like stored in a storing section of 3D glasses worn by the temporally later observer, processing for correcting a 3D observation image in the observation target 3D monitor is performed. Note that, when there are a plurality of observers observing an observation target monitor, the 3D observation image of the observation target 3D monitor only has to be corrected according to a depth information correction value and the like stored in a storing section of 3D glasses worn by an observer having high priority taking into account priority.

On the other hand, in the case of a determination result indicating that the 3D glasses 9J and 9J' are the same 3D glasses (the IDs coincide with each other), in step S59, the 3D monitor 8A or 8B retains data settings of the 3D classes 9J and 9J'. For example, when data of display parameters in displaying a 3D observation image with the display section 43a is stored in the memory 49a in the control section 45a of the 3D monitor 8A, the 3D monitor 8A or 8B retains the data. Therefore, display parameters of the 3D observation image do not change. The same applies in the case of the 3D monitor 8B.

In the case of a determination result indicating that 3D glasses are detected in step S53, as shown in step S56, the 3D monitor 8A or 8B detects 3D glasses 9K' different from the 3D glasses 9J'. In the next step S57, as in the case of step S39, the 3D monitor 8A or 8B performs identification processing for the respective pairs of 3D glasses 9J' and 9K'.

Further, in the next step S58, the 3D monitor 8A or 8B determines, according to determination concerning whether IDs coincide with each other, whether the 3D glasses 9J and 9K detected and identified before and the 3D glasses 9J' and 9K' detected and identified this time are the same 3D glasses. In the case of a determination result indicating that the 3D glasses 9J and 9J' and the 3D glasses 9K and 9K' are not the same 3D glasses, the 3D monitor 8A or 8B returns to the processing in the first step S31. Processing (substantially the same as the processing for the 3D glasses 9J and 9K) is performed on the 3D glasses 9J' and 9K'. That is, when a plurality of observers observe the same monitor, the 3D observation image of the observation target 3D monitor is corrected according to a depth information correction value and the like stored in a storing section of 3D glasses worn by an observer having high priority taking into account priority.

On the other hand, in the case of a determination result indicating that the 3D glasses 9J and 9J' and the 3D glasses 9K and 9K' are respectively the same 3D glasses, in step S59, the 3D monitor 8A or 8B retains data settings of the respective pairs of 3D glasses.

In the next step S60, the 3D monitor 8A or 8B waits for a predetermined time to elapse from time of the processing in step S49. When the predetermined time has elapsed, the 3D monitor 8A or 8B returns to the first step S31 and repeats the same processing.

With the three-dimensional image system 1 in the present embodiment that operates as explained above, in the memories on the respective pairs of 3D glasses side to which the IDs are respectively given, the image parameters such as the depth amount correction values desired by the surgeons acting as the observers using the 3D glasses are stored (saved) (in association with the IDs). Therefore, it is unnecessary to save the image parameters such as the depth amount correction values on the 3D monitors side functioning as the display apparatuses (in association with the IDs). Data management is almost unnecessary or facilitated. The 3D monitor functioning as the display apparatus can display, with a simple configuration, a 3D observation image with image parameters such as a depth amount correction value desired by a surgeon.

In the present embodiment, it is possible to appropriately cope with a case in which, according to a progress or the like of a surgical operation, a position where a surgeon acting as an observer observes the first 3D monitor first changes to a position where the surgeon observes the second 3D monitor different from the first 3D monitor.

More specifically, the respective 3D monitors periodically scan an observation range in which the 3D monitors are observable, detect 3D glasses worn (used) by a surgeon, determine whether the detected 3D glasses coincide with 3D glasses detected and identified before, and make it possible to cope with a result of the determination. Therefore, even when the observation position changes and the observed 3D monitor is changed as explained above, it is possible to observe a 3D observation image with image parameters such as a depth amount correction value desired by the surgeon.

When a plurality of surgeons simultaneously observe one 3D monitor, priority is detected and a 3D observation image is displayed with image parameters such as a depth amount correction value acquired from 3D glasses worn by a surgeon having high priority. Therefore, it is also possible to appropriately cope with a case in which a plurality of surgeons simultaneously observe a 3D monitor. When the processing is performed as shown in FIG. 11, even when (3D glasses of) an observer observing the same monitor changes while a test or a manipulation is performed once, it is possible to appropriately reset a depth amount and the like of the monitor according to the change. Therefore, it is possible to smoothly perform the test or the manipulation.

When a surgeon performs an endoscopic test next time in an environment same as an environment of this time, data in a memory functioning as a storing section of 3D glasses used by the surgeon can be directly used. In other words, for each pair of 3D glasses to which IDs are given, the data in the storing section of the 3D glasses is managed. Therefore, the management of the data is easy and the data can be managed as desired by a surgeon who uses the 3D glasses.

The operation in the case in which the three surgeons Da, Db, and Dc are mainly in the arrangement shown in FIG. 2(A) and FIG. 2(B) is explained.

More specifically, FIG. 2(A) corresponds to
(a) a case in which the first surgeon Da and the third surgeon Dc observe the first monitor 8A and the second surgeon Db observes the second monitor 8B,
FIG. 2(B) corresponds to
(b) a case in which the second surgeon Db and the third surgeon Dc observe the first monitor 8A and the first surgeon Da observes the second monitor 8B. According to the above explanation, it is possible to appropriately cope with the cases (a) and (b).
(c) according to the selection of the priority B in step S44 of FIG. 11, it is possible to appropriate cope with a case in which the first surgeon Da observes the first monitor 8A and the second surgeon Db (the priority B) and the third surgeon Dc (the priority C) observe the second monitor 8B.

Besides the above, arrangements described below are possible:
(d) a case in which the first surgeon Da and the second surgeon Db observe the first monitor 8A and the third surgeon Dc observes the second monitor 8B,
(e) a case in which the second surgeon Db observes the first monitor 8A and the first surgeon Da and the third surgeon Dc observe the second monitor 8B, and
(f) a case in which the third surgeon Dc observes the first monitor 8A and the first surgeon Da and the second surgeon Db observe the second monitor 8B.

It is also possible to cope with such cases substantially in the same manner according to the processing in FIG. 11 by taking into account priority.

It is also possible to cope with the case of surgeons other than the three surgeons in the same manner by taking into account priority. For example, in FIG. 11, the processing is shown in which up to two observers respectively wear 3D glasses and observe one monitor. However, the processing may be applied when three Or more Observers respectively wear 3D glasses and observe one monitor. For example, the processing of glasses detection only has to be performed until 3D glasses different from one another are not detected.

In the operation example explained with reference to FIG. 11 and the like, when an endoscopic test or a manipulation is performed once, the respective 3D monitors include the scanning sections functioning as scanning means for periodically detecting 3D glasses within an observation range and determine, according to IDs, whether 3D glasses detected anew are the same as 3D glasses detected before. However, the determination may be performed according to information concerning distances together with the IDs as explained below.

For example, in the 3D monitor 8A in FIG. 6, it is also possible that, for example, the RF transmitting/receiving section 46a indicated by a dotted line is provided besides the RF transmitting/receiving section 46a, the 3D glasses 9A worn by the surgeon Da acting as the observer are detected by the two RF transmitting/receiving sections 46a, 46a, and a distance La between the 3D monitor 8A and the surgeon Da (or the 3D glasses 9A worn by the surgeon Da) is detected (calculated) using a principle of triangulation. When the surgeon Da changes the distance La and observes the same 3D monitor 8A, it is also possible that depth amount correction values are also respectively set in states of a plurality of distances (also referred to as observation distances) obtained by changing the distance La and the depth amount correction values are also respectively stored in the memory 54a of the 3D glasses 9A according to the distances. The determination concerning the 3D monitor 8A and the surgeon Da is explained above. However, in a period in which an endoscopic test or a manipulation is performed at least once, when one surgeon observes the respective 3D monitors 8A and 8B or when a surgeon having high priority observes the 3D monitors in the case of a simultaneous observation by a plurality of surgeons, data including a depth amount correction value is stored in a memory of 3D glasses together with data of a distance.

As explained above, the respective 3D monitors may periodically perform scans for detecting 3D glasses within the observation range, when 3D glasses are detected anew, determine, according to IDs, whether the detected 3D glasses are the same as 3D glasses detected before, and, when the IDs coincide with each other, further determine whether a detected distance is substantially the same as a distance detected (calculated) before (in other words, whether the distance changes). The 3D monitors desirably retain data of prior image parameters when the detected distance is substantially the same as the distance detected (calculated) before and display, when determining that the distances are different, a 3D observation image reflecting data of image parameters including a depth amount correction value in the case of the distance detected (calculated) anew (temporally later).

Figure 13A:
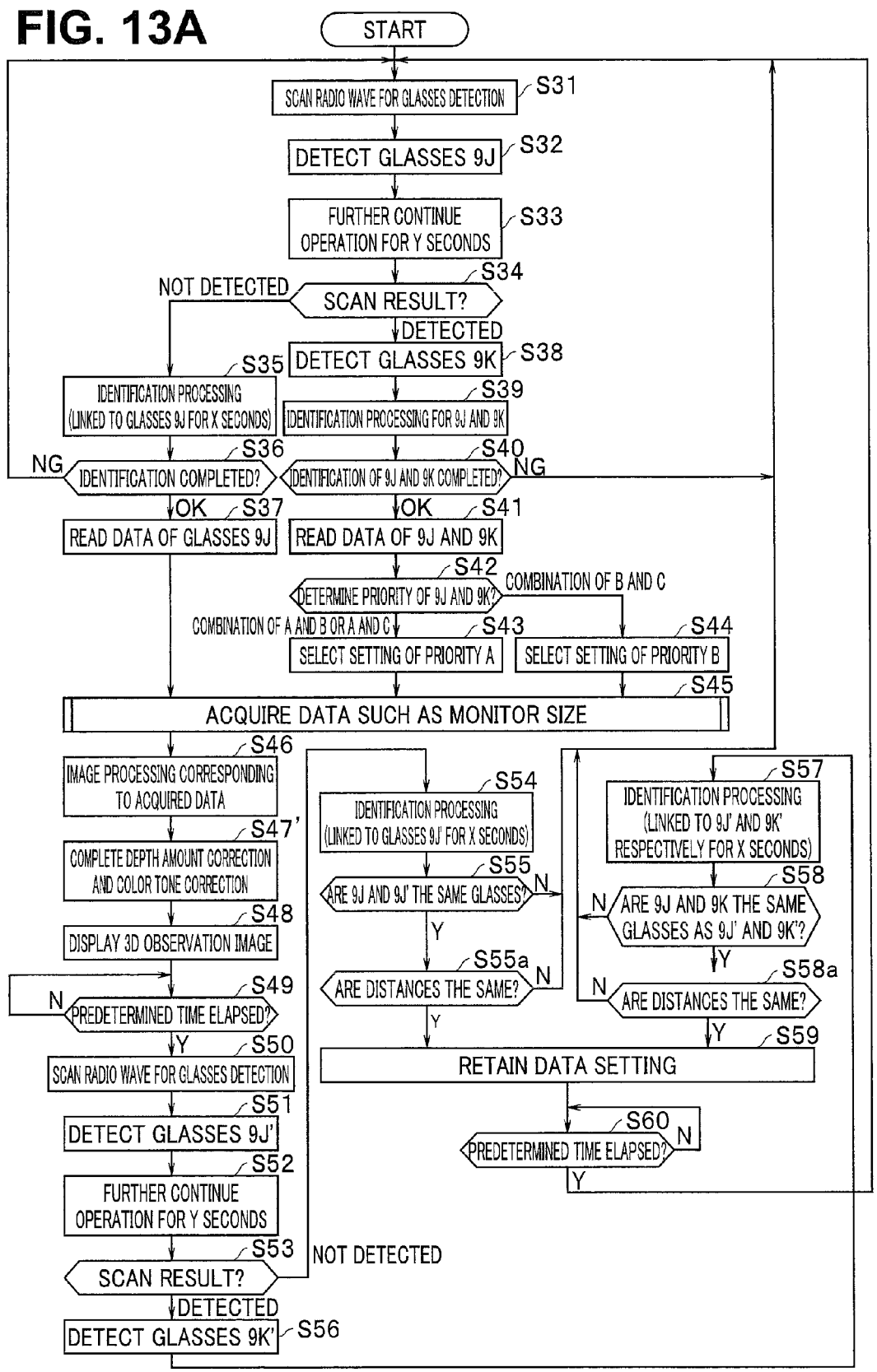
FIG. 13A is a flowchart showing a processing example of a representative operation for detecting a distance between the 3D glasses worn by the surgeon and the 3D monitor and displaying a 3D observation image that reflects a depth amount correction value corresponding to the distance in the first embodiment.

In the case of the setting explained above, an operation corresponding to FIG. 11 is processing shown in FIG. 13A. FIG. 13A corresponds to processing performed when data of a distance L is further stored in the memories of the respective pairs of 3D glasses in FIG. 11. Otherwise, the processing is the same as the processing in FIG. 11. For example, in step S47' in FIG. 13A corresponding to step S47 in FIG. 11, the 3D glasses 9J complete processing of depth amount correction corresponding to the detected (calculated) distance L and complete processing of color tone correction. In step S48, a 3D observation image is displayed with a depth correction amount corresponding to the distance L.

When determining in step S55 that the 3D glasses 9J and 9J' are the same, in the next step S55a, the 3D monitor 8A or 8B determines whether a distance in the case of the detection of the 3D glasses 9J and a distance in the case of the detection of the 3D glasses 9J' are substantially the same. When determining that the distances are substantially the same, the 3D monitor 8A or 8B shifts to step S59. On the other hand, when determining that the distances are substantially different, the 3D monitor 8A or 8B returns to the processing in step S31. According to the processing in step S31, the 3D monitor 8A or 8B changes to a state in which the 3D monitor 8A or 8B reads data of image parameters such as depth amount correction values at the different distances and displays a 3D observation image reflecting the image parameters.

When determining in the determination processing in step S58 that the 3D glasses 9J and 9K are respectively the same as glasses 9J and 9K', in the next step S58a, the 3D monitor 8A or 8B determines whether a distance in the case in which the 3D glasses 9J and 9K are respectively detected and a distance in the case in which the 3D glasses 9J' and 9K are respectively detected are substantially the same (whether the distance changes). When determining that the distances are substantially the same, the 3D monitor 8A or 8B shifts to step S59. On the other hand, when determining that the distances are substantially different, the 3D monitor 8A or 8B returns to the processing in step S31. According to the processing in step S31, the 3D monitor 8A or 8B changes to a state in which the 3D monitor 8A or 8B reads data of image parameters such as a depth amount correction value at the distance detected (calculated) temporally later (in other words, the distance after the change) and displays a 3D observation image reflecting the image parameters. The other processing is the same as the processing in FIG. 11.

When the information concerning the distances are acquired to make it possible to perform depth amount correction corresponding to the distances as explained above, if, because the surgeon acting as the observer changes a position to perform a surgical operation, a distance at which the surgeon observes the 3D monitor changes according to the change of the position, the surgeon is capable of observing a 3D observation image reflecting a depth amount correction value desired by the surgeon in the case of the changed distance. When there are a plurality of observers, it is also possible to appropriately cope with a case in which distances to the plurality of observers change or observers observing the same monitor change. Besides, effects same as the effects explained above are achieved. Note that, in the processing in FIG. 13A, after identifying that the 3D glasses are the same 3D glasses, when determining that the distance changes, the 3D monitor 8A or 8B returns to the first step S31. However, as explained below, the 3D monitor 8A or 8B may display a 3D observation image corresponding to the case of the changed distance without returning to the first step S31.

When the distances are different, that is, when the 3D monitor 8A or 8B temporarily stores (e.g., in a period in which an endoscopic test is performed once) data of depth amount correction values corresponding to a plurality of respective distances in the memory 49a or 49b in the control section 45a or 45b and, for example, when determining in step S55a that the distances are not the same (i.e., the distance changes), the control section 45a or 45b may read out data of a depth amount correction value corresponding to the changed distance from the memory 49a or 49b in the control section 45a or 45b and cause the image processing section 42a or 42b to perform processing for depth amount correction. The display section 43a or 43b may display a 3D observation image reflecting the depth amount correction value corresponding to the changed distance.

In step S58a in FIG. 13A, similarly, without returning to step S31, the control section 45a or 45b may read out data of a depth amount correction value corresponding to the changed distance from the memory 49a or 49b in the control section 45a or 45b and cause the image processing section 42a or 43a to perform processing for depth amount correction. The display section 43a or 43b may display a 3D observation image reflecting the depth amount correction value corresponding to the changed distance.

Figure 13B:
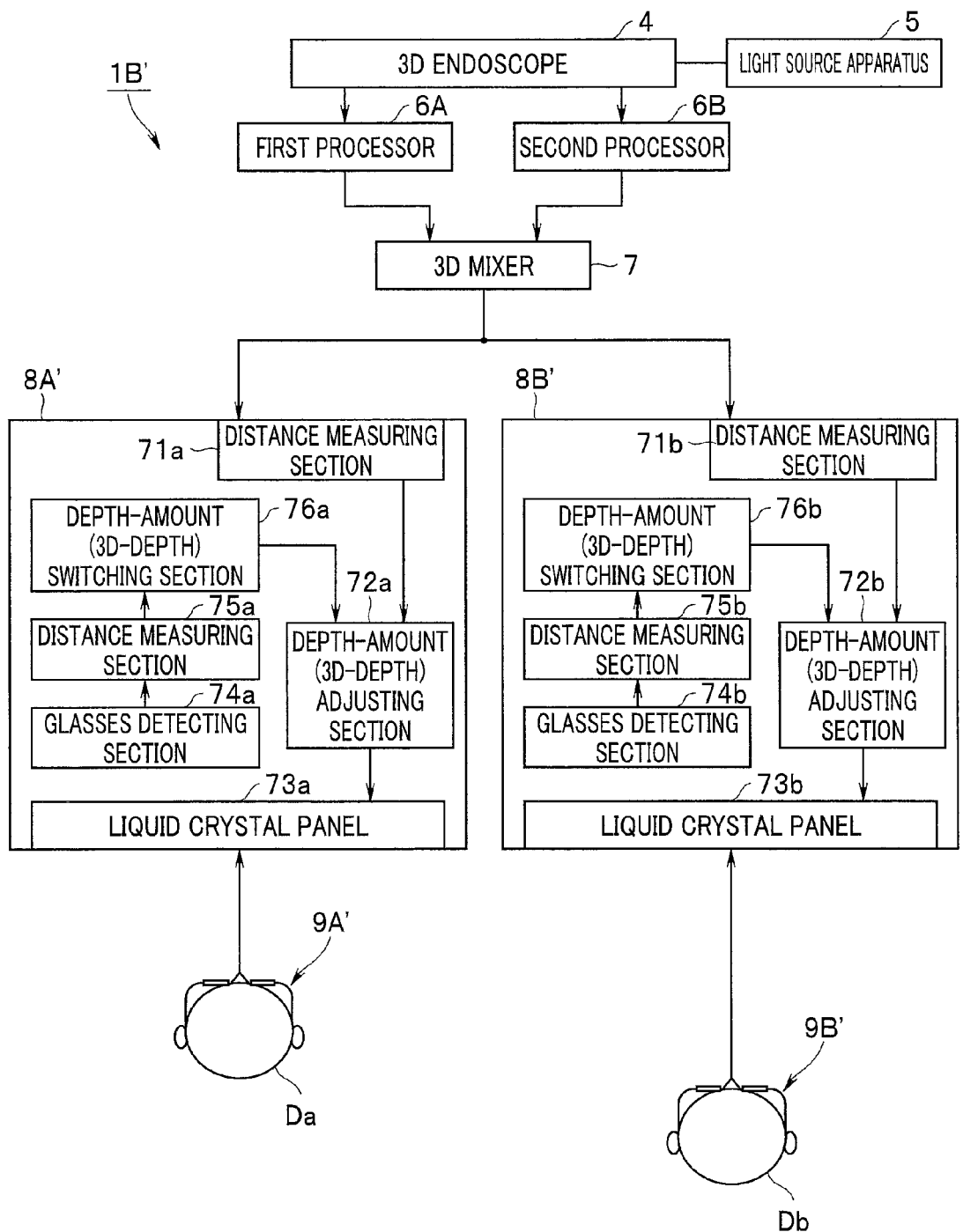
FIG. 13B is a diagram showing an overall configuration of a three-dimensional image system including distance measuring means.

Incidentally, in the three-dimensional image system, a distance between a 3D monitor and a surgeon observing the 3D monitor sometimes changes during a surgical operation. When the distance between the surgeon and the 3D monitor changes, a depth feeling (or a cubic effect) in the case of display of a 3D observation image on the 3D monitor is different from an actual depth feeling (or cubit effect). An observer such as the surgeon sometimes feels a sense of discomfort or tends to have eyestrain. Therefore, as shown in FIG. 13B referred to below, distance measuring means for measuring the distance between the 3D monitor and the observer such as the surgeon may be provided. A depth feeling (or a cubit effect) in displaying a 3D observation image on the 3D monitor may be adjusted according to the measured distance.

A three-dimensional image system 1B shown in FIG. 13B is configured from the 3D endoscope 4, the light source apparatus 5, the first processor 6A, the second processor 6B, the 3D mixer 7, a first monitor 8A', a second monitor 8B', first 3D glasses 9A' worn by a first surgeon, and second 3D glasses 9B' worn by a second surgeon.

The three-dimensional image system 1B shown in FIG. 13B is different from the three-dimensional image system 1 in the first embodiment in configurations of the first monitor 8A', the second monitor 8B', the first 3D glasses 9A' worn by the first surgeon Da, and the second 3D glasses 9B' worn by the second surgeon. The first 3D glasses 9A' and the second 3D glasses 9B' have a configuration not including the memories 54a and 54b in the 3D glasses 9A and 9B.

In the 3D monitor 8A', a 3D video signal inputted to a video input terminal 71a configuring the video input IF 41a in FIG. 3 is inputted to a liquid crystal panel 73a configuring a display section after a depth amount (or 3D depth) is adjusted according to a distance explained below by a depth-amount adjusting section (a depth-amount adjustment circuit) or a 3D-depth adjusting section (a 3D-depth adjustment circuit) 72a.

The 3D monitor 8A' includes a glasses detecting section 74a that detects the first 3D glasses 9A' worn by the first surgeon Da (configured by the RF transmitting/receiving section 46a and the like in FIG. 3). A detection signal of the glasses detecting section 74a is inputted to a distance measuring section (or a distance measuring device) 75a. The distance measuring section 75a measures a distance from the 3D monitor 8A' to the first 3D glasses 9A' worn by the first surgeon Da.

The distance measuring section 75a outputs the measured distance to a depth-amount switching section (or a 3D-depth switching section) 76a. The depth-amount (3D-depth) switching section 76a switches the depth amount (the 3D depth) of the depth-amount adjusting section 72a according to the distance measured by the distance measuring section 75a. Alternatively, the depth-amount adjusting section 72a adjusts, according to the distance measured by the distance measuring section 75a, a depth amount (3D depth) of a 3D image displayed on the liquid crystal panel 73a using the depth amount (the 3D depth) switched by the depth-amount (3D-depth) switching section 76a.

The 3D monitor 8B' has a configuration substantially the same as the configuration of the 3D monitor 8A'. That is, in the 3D monitor 8B', a 3D video signal inputted to a video input terminal 71b configuring the video input IF 41b in FIG. 3 is inputted to a liquid crystal panel 73b configuring a display section after a depth amount (or 3D depth) is adjusted according to a distance explained below by a depth-amount adjusting section (or a 3D-depth adjusting section) 72b.

The 3D monitor 8B' includes a glasses detecting section 74b (configured by the RF transmitting/receiving section 46b and the like in FIG. 3) that detects the second 3D glasses 9B' worn by the second surgeon Db. A detection signal of the glasses detecting section 74b is inputted to a distance measuring section 75b. The distance measuring section 75b measures a distance from the 3D monitor 8B' to the second 3D glasses 9B' worn by the second surgeon Db.

The distance measuring section 75b outputs the measured distance to a depth-amount switching section (a depth-amount switching circuit) or a 3D-depth switching section (a 3D-depth switching circuit) 76b. The depth-amount (3D-depth) switching section 76b switches the depth amount (the 3D depth) of the depth-amount (3D-depth) adjusting section 72b according to the distance measured by the distance measuring section 75b. Alternatively, the depth-amount adjusting section 72b adjusts, according to the distance measured by the distance measuring section 75b, a depth amount (3D depth) of a 3D image displayed on the liquid crystal panel 73b using the depth amount (the 3D depth) switched by the depth-amount (3D-depth) switching section 76b.

Figure 14:
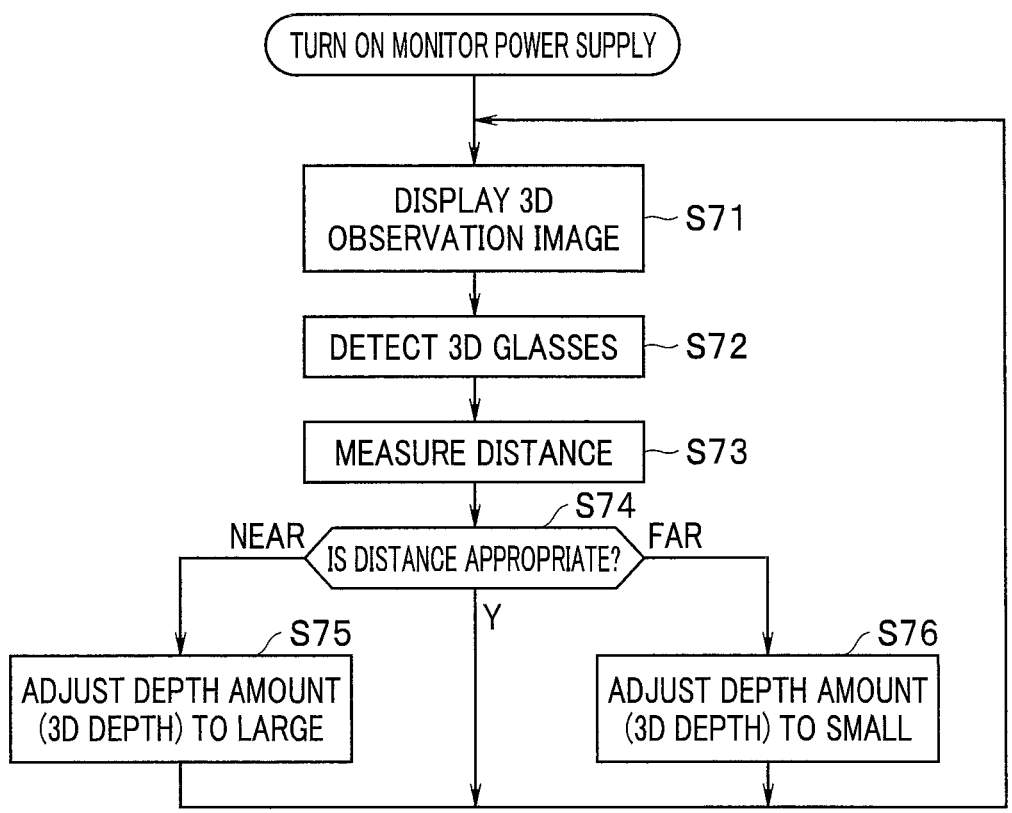
FIG. 14 is a flowchart showing processing of the three-dimensional image system of FIG. 13B.

An operation of the three-dimensional image system 1B in FIG. 13B is explained with reference to a flowchart of FIG. 14. When power supplies of 3D monitors and the like are turned on, as shown in step S71, the 3D monitors 8A' and 8B' respectively display 3D observation images, for example, in a default setting state. As shown in step S72, the glasses detecting sections 74a and 74b in the 3D monitors 8A' and 8B' respectively detect 3D glasses 9A' and 9B' and respectively output detection results to the distance measuring sections 75a and 75b.

As shown in step S73, the distance measuring sections 75a and 75b respectively measure distances from the 3D monitors 8A' and 8B' to the 3D glasses 9A' and 9B' and output the measured distances to the depth-amount (3D-depth) adjusting sections 72a and 72b via the depth-amount (3D-depth) switching sections 76a and 76b.

As shown in step S74, the depth-amount (3D-depth) adjusting sections 72a and 72b determine whether the measured distances are appropriate. When determining that the distances are shorter than appropriate distances, as shown in step S75, the depth-amount (3D-depth) adjusting sections 72a and 72b adjust a depth amount (3D depth) to be larger (or deeper). Thereafter, the operation returns to the processing in step S71.

When determining that the measured distances are longer than the appropriate distances, the depth-amount (3D-depth) adjusting sections 72a and 72b adjust the depth amount (the 3D depth) to be smaller (or shallower). Thereafter, the operation returns to the processing in step S71.

When the measured distances are appropriate, the depth-amount (3D-depth) adjusting sections 72a and 72b do not change (adjust) the depth amount (the 3D depth). The operation returns to the processing in step S71.

In this way, even when the distance at which the surgeon observes the monitor changes, it is possible to display a 3D observation image with a depth amount (3D depth) suitable for the changed distance.

Note that, in the embodiment and the like explained above, embodiments configured by combining components partially different from one another also belong to the present invention. When contents of claims described in original claims do not uniquely coincide with contents described in an original specification, the described contents of the original specification may be corrected to the contents described in the original claims.

In the embodiment explained above, the 3D glasses of a polarizing system are explained as the 3D glasses 9A and 9B. However, 3D glasses of a shutter system may be adopted. In this case, 3D glasses may be adopted in which liquid crystal shutters for the right eye and the left eye are used instead of the polarizing plates 51a and 51b and a driving circuit that alternately switches the liquid crystal shutters for the right eye and the left eye to a transmitting state and a blocking state is provided.

What is claimed is:

1. A three-dimensional image system for multiple 3D display, the three-dimensional image system comprising:
a monitor displaying an image signal as an image for three-dimensional observation;
glasses for three-dimensional observation, the glasses being configured to observe, as a three-dimensional image, the image for three-dimensional observation displayed on a display section of the monitor;
a memory provided in the glasses, the memory storing an image parameter correction value correcting image parameters that cause a cubic effect of the image for three-dimensional observation displayed on the display section;
a transmitter/receiver that scans the glasses including the memory in order to read the image parameter correction value for three-dimensional observation stored in the memory; and
a processor programmed to:
set in the monitor, according to a scanning result of the transmitter/receiver, the image parameter correction value for three-dimensional observation stored in the memory, wherein
the monitor includes first and second display sections disposed in positions different from each other and configuring the display section and first and second monitors respectively including first and second processors configuring the processor,
the glasses for three-dimensional observation include first glasses for three-dimensional observation and second glasses for three-dimensional observation,
the first glasses for three-dimensional observation include a first memory configuring the memory that stores a first parameter correction value for three-dimensional observation and a second image parameter correction value for three-dimensional observation as the image parameter correction value for three-dimensional observation used when the first observer wears the first glasses for three-dimensional observation and respectively observes the first display section and the second display section,
the second glasses for three-dimensional observation include a second memory configuring the memory that stores a third image parameter correction value for three-dimensional observation and a fourth image parameter correction value for three-dimensional observation serving as the image parameter correction value for three-dimensional observation used when a second observer wears the second glasses for three-dimensional observation and respectively observes the first display section and the second display section,
the first processor corrects, with the first image parameter correction value for three-dimensional observation or the third image parameter correction value for three-dimensional observation for which priority order is set higher, the first image parameters for three-dimensional observation in a first image for three-dimensional observation serving as the image for three-dimensional observation displayed on the first display section, to correct a cubic effect of the image for three-dimensional observation displayed on the first display section, and
the second processor performs control to correct, with the second image parameter correction value for three-dimensional observation or the fourth image parameter correction value for three-dimensional observation for which priority order is set higher, the second image parameters for three-dimensional observation in a second image for three-dimensional observation serving as the image for three-dimensional observation displayed on the second display section, to correct the cubic effect of the image for three-dimensional observation displayed on the second display section.

2. The three-dimensional image system for multiple 3D display according to claim 1, wherein the first memory and the second memory store information for determining the priority order for a case in which the first observer and the second observer simultaneously observe the first display section or the second display section.

3. The three-dimensional image system for multiple 3D display according to claim 2, wherein
the first memory is capable of respectively storing color tone information of a display color of images for three-dimensional observation in the first display section and the second display section observed by the first observer, and
the second memory is capable of storing color tone information of a display color of images for three-dimensional observation in the first display section and the second display section observed by the second observer.

4. The three-dimensional image system for multiple 3D display according to claim 2, wherein
the first memory stores the first and second image parameter correction values for three-dimensional observation respectively corresponding to a size of a first display area of the first display section and a size of a second display area of the second display section in a case in which the first observer observes the first display section and the second display section respectively, and
the second memory stores the third and fourth image parameter correction values for three-dimensional observation respectively corresponding to a size of a first display area of the first display section and a size of a second display area of the second display section in a case in which the second observer observes the first display section and the second display section respectively.

5. The three-dimensional image system for multiple 3D display according to claim 1, wherein the processor controls, after correcting, with the first or second image parameter correction value for three-dimensional observation stored in the memory, the first or second image parameters for three-dimensional observation in the first or second image for three-dimensional observation displayed on the first or second display section of the first or second monitor, the transmitter/receiver to periodically perform a scan for detecting the glasses for three-dimensional observation including the memory.

6. The three-dimensional image system for multiple 3D display according to claim 5, wherein
the processor distinguishes, after correcting, with the periodical scan by the transmitter/receiver, the first or second image parameters for three-dimensional observation in the first or second image for three-dimensional observation displayed on the first or second display section,
when glasses for three-dimensional observation are detected anew, whether the glasses for three-dimensional observation are same as the glasses for three-dimensional observation used for the correction of the first or second image for three-dimensional observation and, when the glasses for three-dimensional observation are not the same as the glasses for three-dimensional observation used for the correction,
performs control to correct, with a first or second image parameter correction value for three-dimensional observation stored in the memory of the glasses for three-dimensional observation detected temporally later, the first or second image parameters for three-dimensional observation in the first or second image for three-dimensional observation displayed on the first or second display section.

7. The three-dimensional image system for multiple 3D display according to claim 5, wherein
the processor distinguishes, after correcting, with the periodical scan by the transmitter/receiver, the first or second image parameters for three-dimensional observation in the first or second image for three-dimensional observation displayed on the first or second display section of the first or second monitor,
when glasses for three-dimensional observation are detected anew, whether the glasses for three-dimensional observation are same as the glasses for three-dimensional observation used for the correction of the first or second image for three-dimensional observation and,
when the glasses for three-dimensional observation are not the same as the glasses for three-dimensional observation used for the correction, performs control to correct, with a first or second image parameter correction value for three-dimensional observation stored in the memory of the glasses for three-dimensional observation detected temporally later, the first or second image parameters for three-dimensional observation in the first or second image for three-dimensional observation displayed on the first or second display section and,
when distinguishing that the glasses for three-dimensional observation are the same as the glasses for three-dimensional observation used for the correction, further determines whether a distance for observing the first or second monitor changes and,
when the distance for observing the first or second monitor changes,
performs control to correct, with a first or second image parameter correction value for three-dimensional observation corresponding to the distance after the change, the first or second image parameters for three-dimensional observation in the first or second image for three-dimensional observation displayed on the first or second display section of the first or second monitor.

8. The three-dimensional image system for multiple 3D display according to claim 7, wherein
when the first observer wears the three-dimensional glasses including the memory and changes the distance for observing the first or second monitor, the memory stores a plurality of image parameter correction values for three-dimensional observation, which are different from one another according to a plurality of respective distances different from one another, in association with the respective distances as the image parameter correction value for three-dimensional observation, and
the processor temporarily stores, in a period from a start to an end of an endoscopic test performed once, in a memory provided in the processor, a plurality of first or second image parameter correction values for three-dimensional observation different from one another according to the plurality of distances stored in the memory and, when the distance for observing the first or second monitor changes according to a periodical scan by the transmitter/receiver during the period, performs control to correct, with a first or second image parameter correction value for three-dimensional observation temporarily stored in the memory corresponding to the distance after the change, the first or second image parameters for three-dimensional observation in the first or second image for three-dimensional observation displayed on the first or second display section of the first or second monitor.

9. The three-dimensional image system for multiple 3D display according to claim 1, further comprising:
a stereoscopic endoscope including a left image pickup section and a right image pickup section that pick up optical images of a same object separately on left and right, wherein
an image generating apparatus for generating an image signal of a three-dimensional image for performing a three-dimensional observation generates an image signal of the first or second three-dimensional image according to image processing for alternately displaying, on the first or second display section, left and right two-dimensional picked-up images including a common range in which the left image pickup section and the right image pickup section pick up images in common when the left image pickup section and the right image pickup section pickup images of the same object and a left side range and a right side range in which the left image pickup section and the right image pickup section respectively pick up images of only a left side portion and a right side portion not common to each other in the same object, and
the processor performs control to correct sizes in a left-right direction in the left side range and the right side range in the left image pickup section and the right image pickup section according to the first or second image parameter correction value for three-dimensional observation.

10. The three-dimensional image system for multiple 3D display according to claim 1, wherein the first and second image parameters for three-dimensional observation are first and second depth information for giving respective cubic effects in the first and second images for three-dimensional observation.

* * * * *